(12) United States Patent
Bogdanowicz

(10) Patent No.: US 8,384,904 B2
(45) Date of Patent: Feb. 26, 2013

(54) METHOD AND APPARATUS FOR DETERMINING THE JUNCTION DEPTH OF A SEMICONDUCTOR REGION

(75) Inventor: Janusz Bogdanowicz, Liege (BE)

(73) Assignees: IMEC, Leuven (BE); Katholieke Universiteit Leuven, Leuven (BE)

( * ) Notice: Subject to any disclaimer, the term of this patent is extended or adjusted under 35 U.S.C. 154(b) by 0 days.

(21) Appl. No.: 12/726,173

(22) Filed: Mar. 17, 2010

(65) Prior Publication Data

US 2010/0238449 A1    Sep. 23, 2010

Related U.S. Application Data

(60) Provisional application No. 61/161,001, filed on Mar. 17, 2009.

(51) Int. Cl.
*G01N 21/55* (2006.01)

(52) U.S. Cl. ........................ 356/445; 356/448

(58) Field of Classification Search .......... 356/445–448, 356/432–435, 601, 609, 369, 72, 237.1–237.6; 250/201.2, 559.45, 559.46, 307, 308, 310
See application file for complete search history.

(56) References Cited

U.S. PATENT DOCUMENTS

| | | | |
|---|---|---|---|
| 6,882,424 | B2 | 4/2005 | Opsal et al. |
| 2004/0239945 | A1* | 12/2004 | Borden et al. ............... 356/484 |
| 2005/0122525 | A1* | 6/2005 | Borden et al. ............... 356/445 |
| 2008/0151247 | A1 | 6/2008 | Salnik et al. |
| 2008/0224036 | A1 | 9/2008 | Clarysse et al. |
| 2008/0297189 | A1 | 12/2008 | Everaert et al. |

FOREIGN PATENT DOCUMENTS

| | | |
|---|---|---|
| WO | WO 2006/063809 A2 | 6/2006 |
| WO | WO 2006/063809 A3 | 6/2006 |
| WO | WO 2007/028605 A1 | 3/2007 |

OTHER PUBLICATIONS

Bogdanowicz, et al., Advances in optical carrier profiling through high-frequency modulated optical reflectance, Journal of Vacuum Science and Technology, B 26(1), Jan. 31, 2008, pp. 310-316.
Bogdanowicz, et al., Impact of inactive dopants in chemical vapor deposition layers on photomodulated optical reflectance, Materials Science and Engineering, B 154-155, Dec. 2008, pp. 234-239.
Nicolaides, et al., Nondestructive analysis of ultrashallow junctions using thermal wave technology, Review of Scientific Instruments, vol. 74, No. 1, Jan. 2003, pp. 586-588.
Rosseel, et al., Impact of multiple sub-melt laser scans on the activation and diffusion of shallow Boron junctions, 16th IEEE International Conference on Advanced Thermal Processing of Semiconductors, Sep. 2008.

* cited by examiner

*Primary Examiner* — Tri T Ton
(74) *Attorney, Agent, or Firm* — Knobbe Martens Olson & Bear LLP

(57) ABSTRACT

A method of determining a value of a depth of a semiconductor junction of a substrate using a photomodulated optical reflectance measurement technique is disclosed. In one aspect, the method includes obtaining a substrate which has at least a first region including the semiconductor junction. The method further includes obtaining a reference region. the method further includes performing at least one sequence of: a) selecting a set of measurement parameters for the photomodulated optical reflectance measurement, b) measuring on the at least a first region a first optical signal representative of the substrate with the semiconductor junction using the selected set of parameters, c) measuring on the reference region a second optical signal using the selected set of parameters, and d) determining the ratio of the first optical signal to the second optical signal, and thereafter extracting from the ratio the depth of the semiconductor junction.

22 Claims, 12 Drawing Sheets

METHOD AND APPARATUS FOR DETERMINING THE JUNCTION DEPTH OF A SEMICONDUCTOR REGION

CROSS REFERENCE TO RELATED APPLICATIONS

This application claims priority under 35 U.S.C. §119(e) to U.S. provisional patent application 61/161,001 filed on Mar. 17, 2009, which application is hereby incorporated by reference in its entirety.

BACKGROUND OF THE INVENTION

1. Field of the Invention

The present invention is related to a method and apparatus for determining the doping profile of a doped semiconductor region, in particular a junction depth thereof using photomodulated optical reflectance measurement techniques.

2. Description of the Related Technology

The ITRS roadmap highlights the precise characterization of ultra-shallow junctions, formed by shallow doping of semiconductor regions, as one of the top challenges for sub-32 nm Si-CMOS technologies. Such a junction is typically characterized by a maximum active doping level N and a junction depth N.

The used physical and electrical analytical techniques for determining the maximum doping level and junction depth, such as secondary ion mass spectrometry (SIMS), spreading resistance profiling (SRP), four-point probe (FPP), or alternative candidates, such as scanning spreading resistance microscopy (SSRM) allow an accurate determination of this junction depth $X_j$. However these characterization techniques are destructive and quite slow, e.g. as samples have to be prepared, and therefore prevent any in-line measurement.

Photomodulated optical reflectance (PMOR) is a widely used non-destructive and contactless technique to characterize in a qualitative way the doping profile of such a doped semiconductor region. During measurement, a modulated-power pump laser is directed towards the doped semiconductor region to modify the refractive index profile thereof. This refractive index profile can be modified through generation of excess carriers in the sample, also known as the Drude effect, and/or by temperature effects of the sample under study. Simultaneously a probe laser is directed to this doped semiconductor region where it will be reflected depending on the refractive index profile. By coupling the reflected probe laser signal to a lock-in amplifier, only the variations in the reflectivity of the doped semiconductor sample induced by the modulated pump laser are measured.

An example of such PMOR technique is the Therma-Probe® technique (TP) described in "Non-destructive analysis of ultra shallow junctions using thermal wave technology" by Lena Nicolaides et al. in Review of Scientific Instruments, volume 74, number 1, January 2003. The TP technique is a high-modulation-frequency implementation of the PMOR technique. As the phase shift of the modulated reflected probe laser signal with respect to the pump power laser signal proved to be dependent on the semiconductor doping profile, two independent signals can be obtained from the reflected probe laser signal. These independent signals are labeled as I (in phase) and Q (90° phase difference)

In an embodiment of international patent application WO 2006 063809 titled "Method and device for the independent extraction of the carrier concentration level and electrical junction depth in semiconductor substrate" illustrated by FIGS. 14 and 15, the TP method is used to extract the doping level N and the junction depth $X_j$ of such doped semiconductor sample. To this end two sets of correlation curves are established such that by plotting the pair of independent signals (I,Q) obtained on the doped semiconductor region on these correlation curves, first the maximum doping level N and subsequently the junction depth $X_j$ thereof can be determined.

Although the TP technique allows a non-destructive characterization of a semiconductor doping profile, the variations in the Q signal might prove to be close to the noise level of the measurement to provide a sufficiently accurate value of the junction depth.

SUMMARY OF CERTAIN INVENTIVE ASPECTS

Certain inventive aspects relate to methods and systems for determining the junction depth of a doped semiconductor area using a photomodulated optical reflectance (PMOR) measurement technique. It is an advantage of at least some embodiments of the present invention to provide accurate methods and systems for determining the junction depth of a doped semiconductor area using a photomodulated optical reflectance (PMOR) technique.

It is an advantage of at least some embodiments of the present invention to provide a method or system to extract this junction depth without the need to model the physical phenomena impacting the refractive index profile and to apply this model to the measured signals.

It is an advantage of at least some embodiments of the present invention to provide a method or system to extract the junction depth whereby the extracted junction depth is in very good correlation with the junction depth obtained by SIMS.

It is an advantage of at least some embodiments of the present invention to provide a method or system to extract this junction depth with sub-nm reproducibility for depths ranging from about 15 to 30 nm.

It is an advantage of at least some embodiments of the present invention to provide a method or system to extract an absolute value of this junction depth while providing an inherent check on the fitness of the measured data for the extraction procedure.

It is an advantage of at least some embodiments of the present invention to provide a method or system to extract a relative value of this junction depth while providing an inherent check on the fitness of the measured data for the extraction procedure. Such method may be of particular relevance to assess the variation of an unknown semiconductor profile as formed in different regions of a substrate.

One aspect relates to a method of determining a value of a depth of a semiconductor junction of a substrate using a photomodulated optical reflectance measurement technique, the method comprising obtaining a substrate having at least a first region comprising the semiconductor junction, obtaining a reference region. The method further comprises performing at least one sequence of (a) selecting a set of measurement parameters for the photomodulated optical reflectance measurement, (b) measuring on the at least a first region a first optical signal representative of the substrate with the semiconductor junction using the selected set of parameters, (c) measuring on the reference region a second optical signal using the selected set of parameters, and (d) determining the ratio of the first optical signal to the second optical signal, and thereafter extracting from the ratio the depth of the semiconductor junction.

According to certain embodiments of the present invention determining the value of the depth of the semiconductor junction comprises determining the absolute value of the depth of the semiconductor junction.

According to certain embodiments of the present invention the substrate comprises at least a second region not comprising the semiconductor junction, wherein the reference region is the second region.

According to certain embodiments of the present invention, the substrate is a bulk semiconductor substrate having a first major surface comprising the junction and a second major surface without the junction, whereby the first optical signal being measured on the first major surface, and, the second optical signal being measured on the second major surface.

According to certain embodiments of the present invention the second optical signal is measured on the substrate prior to forming the junction, and the first optical signal is measured on the substrate after the junction has been formed in the substrate.

According to certain embodiments of the present invention obtaining the reference region comprises providing another substrate without junction, the optical and semiconducting properties of this other substrate being substantially equal to the substrate with junction, the first optical signal being measured on the substrate with junction, and, the second optical signal being measured on the substrate without junction.

According to certain embodiments of the present invention the depth of the semiconductor junction is extracted from the ratio with the formula:

$$X_j = \frac{\cos^{-1}(R_a)\lambda_{probe}}{4\pi n_o}$$

with $X_j$ being the junction depth, $\lambda_{probe}$ being the optical wavelength of a laser beam used for probing the sample, $n_o$ being the refractive index of the substrate in the absence of free carriers and $R_a$ being the ratio of the first optical signal to the second optical signal.

According to certain embodiments of the present invention the reference region consists of another region of the substrate comprising the semiconductor junction, the another region being different from the first region, and determining the value of the depth of the semiconductor junction comprises determining the relative value of the depth of the semiconductor junction.

According to certain embodiments of the present invention the depth of the semiconductor junction is extracted from the ratio with the formula:

$$\frac{\Delta R/R^l_{layer}}{\Delta R/R^l_{reference}} \rightarrow \frac{\cos\left(\frac{4\pi n_0 X_j}{\lambda}\right)}{\cos\left(\frac{4\pi n_0 X_j^{reference}}{\lambda}\right)}$$

with $X_j$ being the junction depth and $X_j^{reference}$ being the junction depth in the reference region, $\lambda$ being the optical wavelength of a laser beam used for probing the sample, $n_o$ being the refractive index of the substrate in the absence of free carriers, $\Delta R/R_{layer}$ being the photomodulated optical reflectance signal in the first region and $\Delta R/R_{reference}$ being the photomodulated optical reflectance signal in the reference region.

According to certain embodiments of the present invention measuring the first and/or second optical signal representative of a substrate comprises providing a pump laser beam, providing a probe laser beam, focusing the pump laser beam to a spot on the substrate, the pump laser beam modulating in an area of the substrate the refractive index profile thereof, focusing the probe laser beam to another spot on the substrate and measuring a predetermined characteristic of the probe laser beam reflected by the photomodulated area.

According to certain embodiments the present invention the set of parameters comprises an offset d between the two spots on the substrate to which the pump laser beam and the probe laser beam are respectively focused.

According to certain embodiments of the present invention the sequence of processes i) to iv) are repeated by selecting another value for the offset d.

According to certain embodiments of the present invention the sequence of processes i) to iv) is repeated for increasing values of the offset d, until the ratio converges to a value between 1 and −1.

According to certain embodiments of the present invention measuring a predetermined characteristic of the reflected probe laser beam comprises measuring a component of the reflected probe laser beam which is in phase with the pump laser beam.

According to certain embodiments of the present invention the semiconductor junction is formed adjacent to a surface of the substrate, the method further comprising reducing the carrier recombination at the surface, such that during the measurement the first optical signal converges and the second optical signal converges. This reduction in carrier recombination can be obtained by preventing free carriers from reaching the illuminated surface due the presence of an electrical field of electrostatic potential at this surface. This reduction in carrier recombination can be obtained by preventing recombination at the surface, i.e. by reducing the interface traps at the surface.

According to certain embodiments of the present invention the set of parameters of the PMOR measurement can be, apart from the offset d, also the time interval during which the first and the second optical signal are measured, and whereby the respective time intervals are selected such that during the measurement the first optical signal converges and the second optical signal converges.

According to certain embodiments of the present invention the substrate is a semiconductor layer.

Another inventive aspect relates to a method of determining the absolute value of the depth of a semiconductor junction formed in a substrate using a photomodulated optical reflectance measurement technique. The method comprises performing at least one sequence of: i) selecting a set of measurement parameters for the photomodulated optical reflectance measurement, ii) measuring a first optical signal representative of the substrate with the semiconductor junction using the selected set of parameters, iii) measuring a second optical signal representative of only the semiconductor substrate using the selected set of parameters, iv) determining the ratio of the first optical signal to the second optical signal, and thereafter extracting from the ratio the depth of the semiconductor junction.

Another inventive aspect relates to a method of determining the relative value of the depth of a semiconductor junction formed in a region of a substrate using a photomodulated optical reflectance measurement technique, the method comprising providing a substrate having at least two regions comprising the semiconductor junction. The method further comprises performing at least one sequence of: i) selecting a set of measurement parameters for the photomodulated optical reflectance measurement, ii) measuring on one of these regions a first optical signal representative of the substrate with the semiconductor junction, iii) measuring on another one of these regions a second optical signal representative of the semiconductor substrate with the semiconductor junction using the selected set of parameters, iv) determining the ratio of the first optical signal to the second optical signal, and thereafter extracting from the ratio the relative depth of the semiconductor junction.

Another inventive aspect relates to a method of determining the depth of a semiconductor junction formed in at least one region of a substrate using a photomodulated optical reflectance (PMOR) technique, which PMOR technique comprises: providing a substrate to be measured, providing a pump laser beam, providing a probe laser beam, focusing the pump laser beam to a spot on the substrate to be measured, the pump laser beam modulating in an area surrounding this pump laser beam spot the refractive index profile of the underlying substrate to be measured, focusing the probe laser beam on the substrate to be measured at on offset d from the pump laser beam spot, and measuring a predetermined characteristic of the probe laser beam reflected by the photomodulated area. The method comprises performing at least one sequence of i) performing a PMOR measurement on the junction region to measure a first predetermined characteristic representative of the substrate with the semiconductor junction, ii) repeating this PMOR measurement to measure a second predetermined characteristic representative of at least the substrate without the semiconductor junction, iii) determining the ratio of the first predetermined characteristic to the second predetermined characteristic, and, thereafter extracting from the ratio the depth of the semiconductor junction.

Another inventive aspect relates to an apparatus for determining the absolute value of the depth of a semiconductor junction formed on a first major surface of a substrate, the substrate further comprising a second major surface, the apparatus comprising a pump laser beam, a probe laser beam, means for focusing the pump laser beam to a spot on the first major surface of the substrate thereby modulating in an area surrounding this pump laser beam spot the refractive index profile of the underlying substrate, means for focusing the probe laser beam on the first major surface of the substrate at on offset d from the pump laser beam spot, and means for measuring a predetermined characteristic of the probe laser beam reflected by the photomodulated area on the first major surface, wherein the apparatus further comprises: means for focusing the pump laser beam and the probe laser beam also to the second major substrate, and, means for measuring a predetermined characteristic of the probe laser beam reflected by the photomodulated area on the second major surface.

According to embodiments of the present invention the apparatus further comprising a means for varying the offset between the probe laser beam and the pump laser beam at respectively the first major surface and the second major surface of the substrate.

BRIEF DESCRIPTION OF THE DRAWINGS

The drawings described are only schematic and are non-limiting. In the drawings, the size of some of the elements may be exaggerated and not drawn on scale for illustrative purposes. The dimensions and the relative dimensions do not correspond to actual reductions to practice of the invention.

DETAILED DESCRIPTION OF CERTAIN ILLUSTRATIVE EMBODIMENTS

Figure 1:
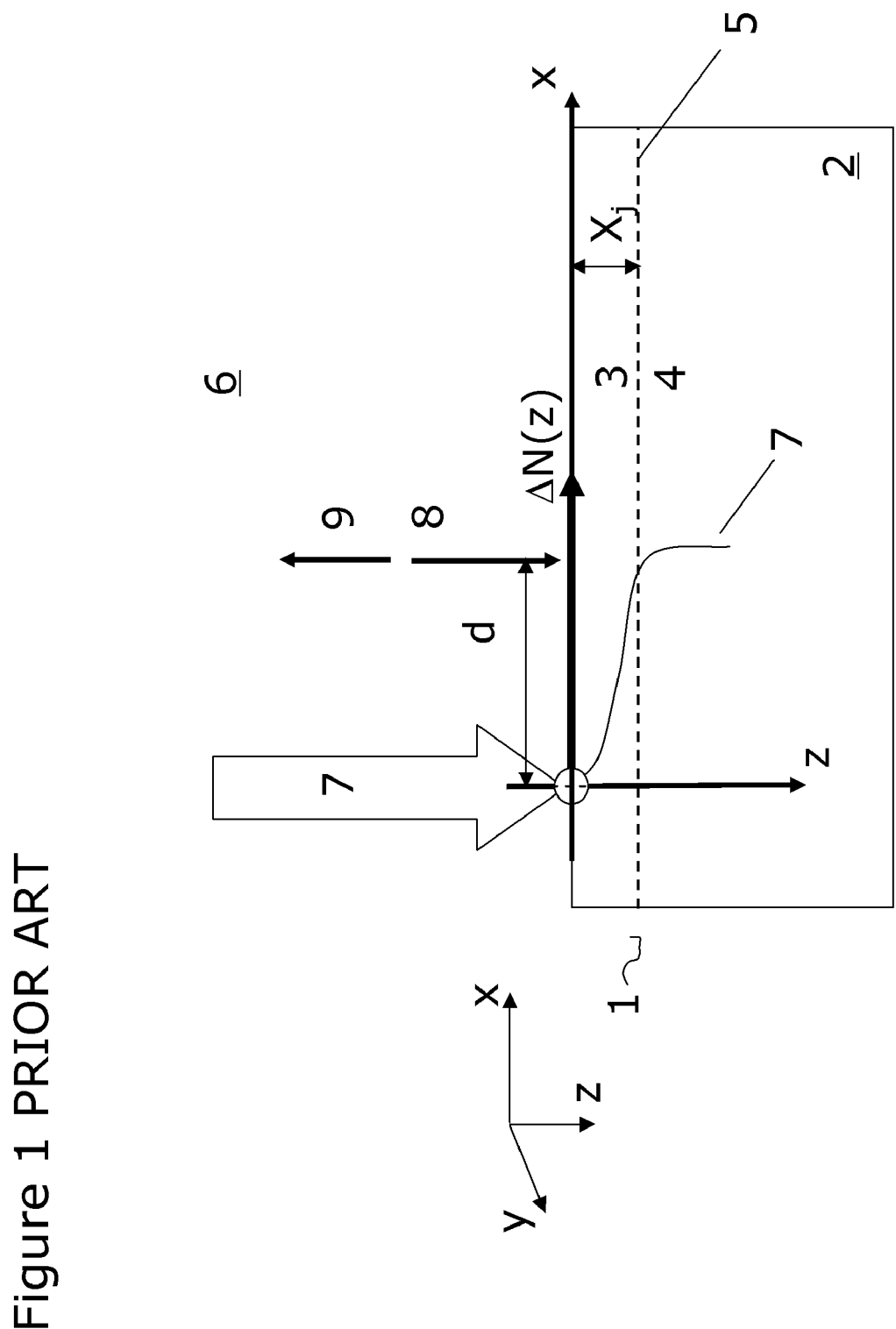
FIG. 1 illustrates a schematic representation of the operation principle of known photomodulated optical reflectance (PMOR) techniques.

The present invention will be described with respect to particular embodiments and with reference to certain drawings but the invention is not limited thereto but only by the claims.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

For the purpose of teaching, the Therma-Probe® method (TP) is used to measure the semiconductor region, although the invention is not limited to this particular PMOR method. The Therma-Probe® technique (TP) is described in international patent application WO2007028605 titled "A method and device to quantify active carrier profiles in ultra-shallow semiconductor structures", in United States patent application US 2008/0224036 paragraphs 8 to 12 and each of which is hereby incorporated by reference in its entirety. The next paragraph provides a schematic of the operation principle of such PMOR technique. In the examples provided below, a TP630XP tool from KLA-Tencor was used to perform the PMOR measurements, embodiments of the present invention not being limited thereby.

FIG. 1 shows a sample 1 comprising a substrate 2 of a semiconducting material. Where in embodiments of the present invention reference is made to substrate, reference is made to the region of interest, and other parts or supporting layers may also be present without reference being made thereto. The sample 1 can be a bulk semiconductor substrate such as a silicon or germanium wafer, optionally comprising layers of semiconductor material such a Ge, SiGe or III-V materials such as GaAs, InP, . . . . These layers are then formed at least in a selected area on a main surface of this semiconductor substrate. The semiconductor substrate 2 can thus be a part of the bulk semiconductor substrate exposed at a main surface thereof or can be the stack of the one or more optional semiconducting layers on this semiconductor substrate. Instead of having a substrate with a substantially homogeneous composition, one can have a sample formed as a stack of semiconductor and dielectric layers such as a silicon-on-insulator substrate (SOI) or germanium-on-insulator substrate (GOI) whereby a semiconducting layer is isolated from the semiconductor substrate by a dielectric layer. The semiconductor substrate 2 is then the layer formed on this isolating dielectric layer. The semiconducting substrate 2 can optionally be formed as a stack of one or more semiconducting layers. These one or more layers are then formed at least in a selected area on a main surface of this isolating dielectric layer.

The semiconductor substrate 2 typically comprises an upper doped layer 3 formed on a lower undoped or lower doped layer 4. The doping profile of a doped layer can be characterized by a maximum active doping concentration $N_{active}$ and a vertical extension or depth $X_j$. The as-formed or as-implanted doping profile will differ from the active doping profile because the number of doping atoms that provides a free carrier depends inter alia on the thermal budget applied to the doped layer. Hence the active doping concentration will be equal to or less than the as-implanted doping concentration as a part of the doping atoms remains inactive. As will be discussed later on, only the activated doping atoms contribute to the PMOR signal. The layer 3 can be formed by depositing an in-situ doped layer 3 on top of layer 4, yielding a uniform doping profile over the layer 3, also known as box-profile. Chemically Vapor Deposition (CVD) or epitaxial layer growth are known techniques to form a doped layer on a substrate. Alternatively the doped layer 3 can be formed by implanting dopants into the substrate 2, yielding a doped layer 3 and a remaining undoped layer 4. By using e.g. ion implantation for implanting dopants into the substrate 2, any kind of doping profile can be obtained depending on the choice of implant species, the energy and implantation dose used. Layer 3 can be doped with a dopant of the same or the opposite type of dopant used to dope the underlying layer 4. In the latter case a junction 5 is created between upper layer 3 and underlying layer 4. As this junction 5 is located at a given depth in the substrate 2, this junction can be characterized by a junction depth $X_j$. Examples of such doped layers 2 are the source or drain junction of a transistor such as a field effect transistor, the emitter region of a bipolar transistor.

A photomodulated optical reflectance (PMOR) measurement typically comprises the following processes. A pump laser beam 7 and a probe laser beam 8 impinge from the surroundings 6 on the substrate 2. The incident probe laser beam 8 and the reflected probe laser signal 9 are indicated by respectively arrows 8 and 9. The pump laser beam 7 will cause a variation in the refractive index profile of the substrate 2, typically by generating an excess carrier profile $\Delta N(z)$ in this substrate 2. The pump laser 7 thus has a wavelength (optical frequency) providing energy quanta larger than the bandgap of the semiconductor material under study such that excess carriers can be generated in this semiconducting material when it is optically stimulated by the pump laser 7. The pump laser beam 7 typically consists of a time-independent component (DC) and a time varying component (AC). In case of TP this time varying component of the pump laser beam 7 has a modulation frequency of about 1 MHz and an optical wavelength of about 790 nm. In FIG. 1, the excess carrier profile $\Delta N(z)$ as function of depth z into the substrate 2 is also shown, indicated by graph 7. The wavelength (optical frequency) of the probe laser 8 is selected to only generate no or only a negligible amount of excess carriers when incident on the semiconductor layer under study. In case of TP the optical wavelength of the probe laser beam 3 is typically 670 nm. The probe laser beam arrow 8 will be reflected, thus generating the reflected probe laser signal arrow 9 at various positions on the semiconductor substrate 2. For example, the probe laser beam 8 may be reflected at the surface, yielding a surface component in the reflected probe laser signal 9. It may also be reflected by a change in the excess carrier profile which can occur at the surface, yielding a near-surface component, or at the interface between the doped part 3 and undoped part 4 on the gradient of N(z), yielding an interface component. The probe laser beam may also be reflected at any transition in the doping profile.

Typically, both lasers, pump laser 7 and probe laser 8, are in a fixed measurement set-up and both incident laser beams have a direction perpendicular to the layer surface, meaning incident at a zero angle relative to the layer surface normal. The maximum power and the time modulation frequency of the pump laser 7 are typically constant. Also the time during which the reflected probe laser beam 9 or a component thereof is measured is typically kept constant. The spacing d between the probe laser 8 and the pump laser 7 can be varied as illustrated in FIG. 1. A small or zero offset or laser separation, i.e. both laser beams 7, 8 impinging on substantially the same spot on the semiconductor substrate 2, corresponds to a maximum number of excess carriers being probed by the probe laser 3 thereby yielding a high reflected signal. One can also determine the reflected probe signal 9 as function of the offset d between the pump laser beam 7 and the probe laser beam 8 as incident on an exposed surface of the semiconductor substrate 2. The curve showing a signal of the reflected probe laser 9 as function of this offset d for a given sample and fixed measurement conditions is known as offset curve or tracker scan.

According to the disclosure one can determine the depth $X_j$ of a semiconductor junction 5 by performing a first PMOR measurement on a test sample 1 of this semiconductor junction and by repeating this PMOR measurement on a reference sample. By making the ratio $R_a$ of the outcome of both PMOR measurements one obtains a signal that is proportional to this junction depth $X_j$. Both PMOR measurements are performed using the same PMOR measurement conditions.

During the PMOR measurement the probe laser beam 8 and the pump laser beam 7 are spaced apart from each other such that these beams impinge on different spots on the surface of the sample 1. As will be shown later, by performing the PMOR measurement with an offset d>0, the reflected probe laser beam signal 8, or the component thereof that is measured, will be dominated by the substrate plasma wave component. The layer plasma wave component and the thermal wave component will become negligible, even more with increasing offset d.

The PMOR signal obtained on the test sample 1 is thus an optical signal representative of the semiconductor junction 5 including the substrate 2 in which this junction 5 is formed.

Depending on the reference sample, the ratio of both PMOR measurements yields the absolute or the relative value of this junction depth $X_j$. If the reference sample is chosen as to yield an optical signal representative of only the substrate 2 in which the junction 5 is formed without containing the junction 5 itself, then the absolute value of the junction depth can be extracted from the ratio $R_a$ of both PMOR measurements. If the reference sample is chosen as to yield also an optical signal representative of the semiconductor junction 5 including the substrate 2 in which this junction 5 is formed, then the relative value of the junction depth $X_j$ can be extracted from the ratio $R_a$ of both PMOR measurements. In this case one can only determine the difference in junction depth $\Delta X_{j\_} = (X_{j\_test} - X_{j\_reference})$ between the actual junctions formed in respectively the test sample 1 and the reference sample without knowing the absolute value of this junction depth $X_j$.

The selection of the parameters of the PMOR measurement in order to obtain a reflected optical signal mainly or only containing the substrate plasma wave component is determined by the rate at which the layer plasma wave component and the thermal wave component decay with the position x along the surface of the sample, with x=0 at the spot where the pump laser beam is incident on the surface of the sample.

Figure 2:
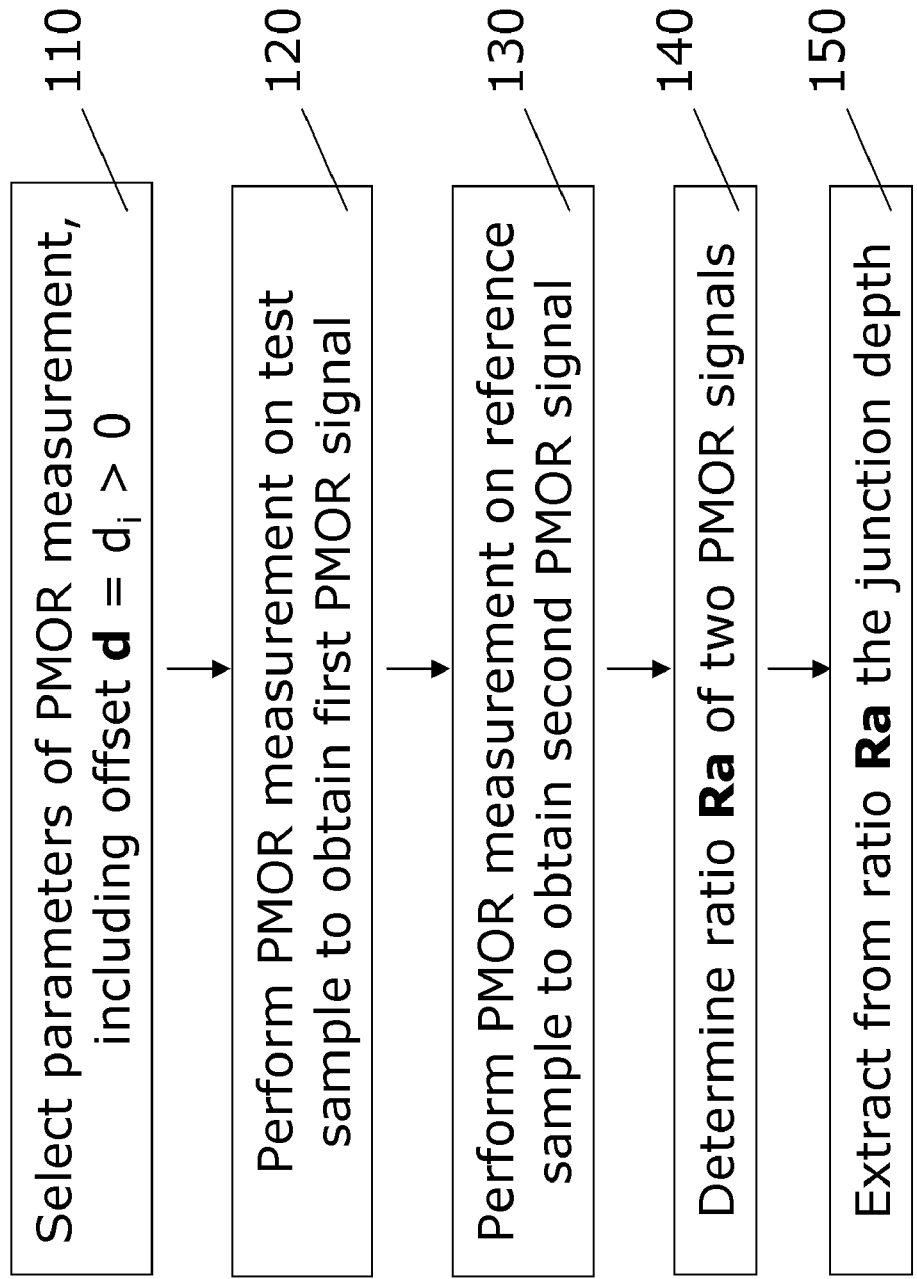
FIG. 2 is a flowchart illustrating a method for extracting the junction depth according to an embodiment of the present invention.

FIG. 2 shows a flow chart listing different processes of the extraction method 100 as disclosed. First the parameters of the PMOR measurement are selected 110. This parameter set includes the offset d, the pump laser settings such as optical frequency, modulation frequency and power and the probe laser settings such as optical frequency. As explained in this disclosure the offset d is selected to obtain a PMOR signal in which the layer 3 plasma wave component and the thermal wave component are absent or at least negligible compared to the layer 4 plasma wave component, e.g. less than about 10%, particularly less than about 1% of the latter signal. The settings of the pump laser parameters are selected in view of the band gap of the semiconductor material, the penetration depth and the desired plasma and thermal wave amplitudes and lateral extensions. The optical frequency of the probe laser is selected in view of the semiconductor material and junction depth. A PMOR measurement with the selected parameters is performed on the actual junction to be characterized 120. This measurements yields a PMOR signal that is representative of the junction 5 and the substrate 2 in which/or on which 4 the junction is formed. This PMOR measurement is repeated 130 on a reference sample as to obtain a signal that is representative for the substrate 2 only if an absolute value of the junction depth is to be obtained, otherwise this PMOR measurement can also be repeated on a reference sample to generate a PMOR signal that is representative for the junction 5 and the substrate 4 such that a relative difference between the junction depth of the test sample and the reference sample can be made. One can choose to first measure the test sample or first measure the reference sample. Once both PMOR signals are obtained the ratio of the PMOR test sample signal to PMOR reference sample signal is made 140. From this ratio $R_a$ one can derive 150 the absolute value or the relative value of the junction depth of the test sample depending on the reference sample used.

Figure 3:
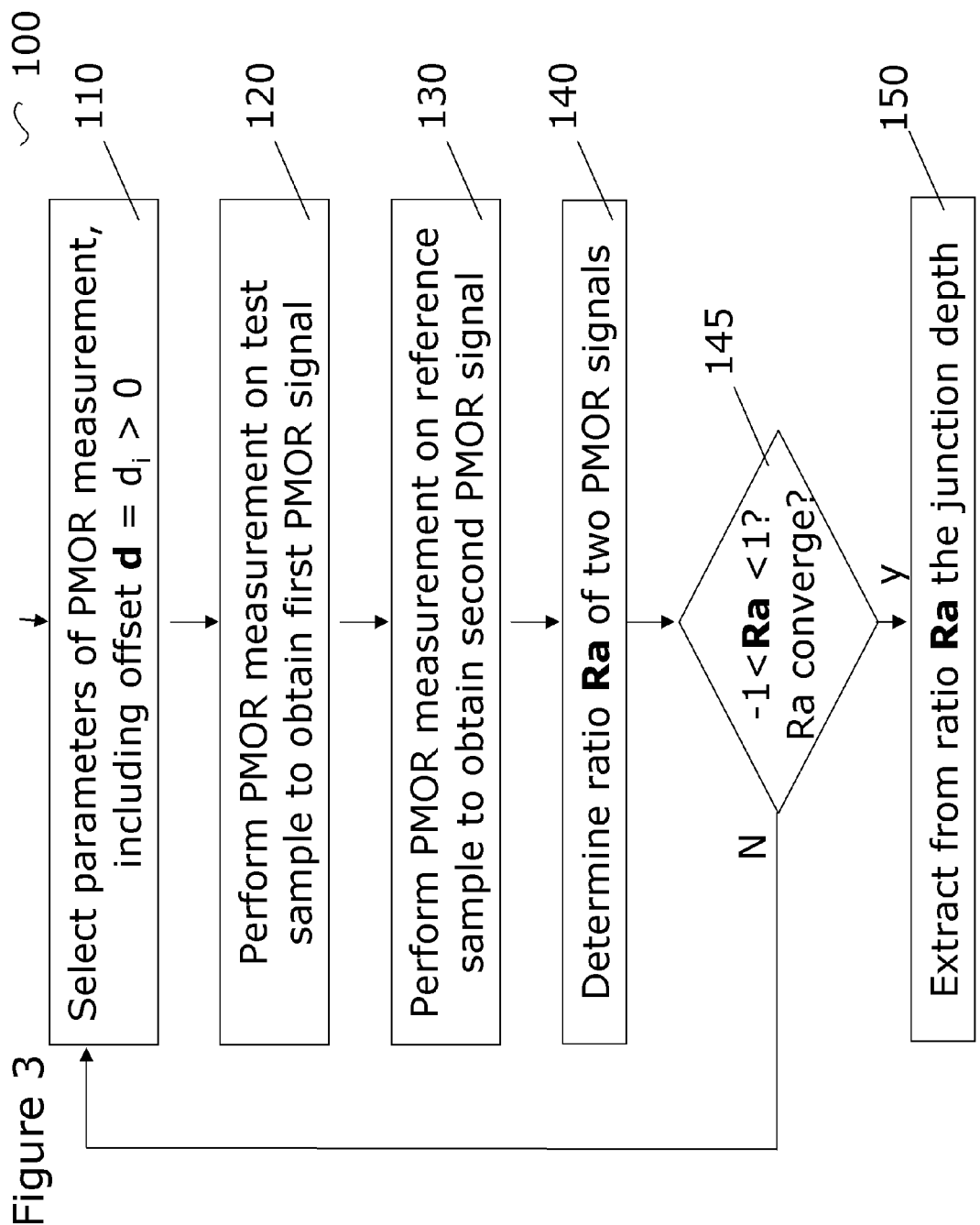
FIG. 3 is a flowchart illustrating a method for extracting the junction depth according to another embodiment of the present invention.

FIG. 3 illustrates a variant to the extraction method illustrated by FIG. 2. It adds the process of validating the measured ratio $R_a$ 145. A first check is to see if this ratio has a value which is consistent with the expected cosine behavior thereof, i.e. if the value is within the [−1,1] range. If this is not the case one can not use the measured ratio either because the selected PMOR measurement parameters are inappropriate, e.g. incorrect optical frequency of the probe laser, or because the samples used do not generate PMOR signals in line with the assumptions made in this disclosure, e.g. a low activation degree of the as-formed doping profile. In the first case one can select another PMOR parameter set and perform another PMOR measurement to see if a relevant value for the PMOR signal ratio can be obtained for the given samples. If the ratio $R_a$ does yield a value between −1 and 1, one can also check if this value changes with the offset d. Ideally one needs only one value of the offset d which is sufficiently large to limit the contribution of the layer 3 plasma wave component and the thermal wave component to the overall PMOR signal. A minimal value of d can be determined if the physical characteristics of the substrate 2 are known: the decay of the thermal wave is dependent on the type of semiconductor material, while the decay of the layer 3 plasma wave component is faster than of the substrate 2, the latter can also be determined if the substrate is known. To be on the safe side one can perform at least two PMOR measurements on the sample, but with a different value of the offset d to check if the obtained PMOR is stable or changes with the offset d. One can even choose to perform several PMOR measurements by moving the probe laser 8 relative the pump laser 9 during the PMOR measurement, either continuously or in discrete steps.

In the following paragraphs, the physics underlying certain illustrative embodiments of the methods disclosed in this description is explained using the TP method for illustration.
Section 1: Theory of PMOR on Active Doping Profiles First it is summarized how to derive an approximate formula to explain the behavior of the PMOR signals on box-like active doping profiles 3. The theory is then generalized to account for the lateral behavior of the PMOR signal, i.e. when the pump 7 and the probe 8 laser beams are separated with an offset d.

As explained in the preceding paragraphs, PMOR is an optical technique using two lasers. First, as the pump laser 7 has photon energy higher than the bandgap of the semiconductor material of the substrate 2, it will generate upon irradiation not only an excess temperature distribution, but also an excess carrier distribution in the substrate 2. As the power of the pump laser beam 7 is modulated with time, also the temperature and the excess carrier distributions will vary periodically with time. The probe laser 8 is reflected on the sample by the change in the refractive index profile caused by this time-dependent temperature and excess carrier distribution resulting in its turn in a time-dependent reflected probe laser beam 9. The detected reflected probe laser beam 9 is coupled to a lock-in amplifier which records it with very high sensitivity.

As disclosed by J. Bogdanowicz in "Impact of inactive dopants in chemical vapor deposition layers on photomodulated optical reflectance" in Materials Science & Engineering B, 154-155 (2008) p 234-239, hereby incorporated by reference in its entirety, the PMOR signal $\Delta R/R$ can be expressed in the case of a box-like active doping profile 3 with junction depth $X_j$ and active doping concentration $N_{active}$, to vary as.

$$\frac{\Delta R}{R} = \frac{4}{n_0^2 - 1} \left\{ -\frac{|\beta|}{m_e + m_h} \left[ \underbrace{\left(1 - \cos\left(\frac{4\pi n_0 X_j}{\lambda}\right)\right) \frac{\Delta N_{substrate}^2}{N_{active}}}_{\text{layer}} + \underbrace{\cos\left(\frac{4\pi n_0 X_j}{\lambda}\right) \Delta N_{substrate}}_{\text{substrate}} \right] + \underbrace{\delta \Delta T_{surface}}_{\text{temperature}} \right\} \quad [1]$$

where $m_e$ and $m_h$ are respectively the electron and hole effective masses, $n_0$ is the substrate 2 lattice refractive index, i.e. without any free carriers, at the probe laser 8 optical wavelength $\lambda$, $\beta = -m\partial n/\partial N$ is the Drude coefficient accounting for the variations in the refractive index n of the substrate 2 due to the presence of excess free carriers having effective mass m, and where $\delta = \partial n/\partial T$ accounts for the variations in this refractive index n due to the temperature T rise. $\Delta T_{surface}$ is the excess temperature at the surface of the substrate 2, $\Delta N_{substrate}$ is the excess carrier concentration in the bottom layer 4 of the substrate 2, $\Delta N^2_{substrate}/N_{active}$ is the excess carrier concentration in the upper layer 3 of the substrate 2 if the following assumptions are made: Boltzmann statistics being applicable, no bandgap narrowing present, the quasi-Fermi levels being substantially constant through the space-charge regions and that $\Delta N_{substrate} \ll N_{active}$.

The above formula [1] shows that the PMOR signal $\Delta R/R$ is composed of three components related respectively to the excess carrier concentration in the upper layer 3 (layer plasma component), to the excess carrier concentration in the lower layer 4 (substrate plasma component) and, to the excess temperature (thermal component). Interestingly, formula [1] also shows directly how the PMOR signal $\Delta R/R$ depends to the doping concentration $N_{active}$ and the junction depth $X_j$.

Formula [1] describes the behavior of the PMOR signal $\Delta R/R$ when the probe 8 and the pump 7 laser beams are coincident on the surface of the substrate 2. In this description however the lateral behavior of the PMOR signal $\Delta R/R$, is disclosed. How does the measured signal of the reflected probe laser beam 9 vary when the spot of incidence of the probe laser beam 8 is moved along the x-axis relatively to the spot of incidence of the pump laser beam 7, i.e. when the two laser spots are separated from each-other with an offset d. As a first approximation, it is assumed that the upper layer 3 plasma component, the lower layer 4 plasma component and the thermal component all decay exponentially with respective decay lengths $L_{layer}$, $L_{substrate}$, and $L_{thermal}$. For the total PMOR signal $\Delta R/R$ the following relationship can be determined:

$$\frac{\Delta R}{R}(x) = \frac{4}{n_0^2 - 1} \left\{ -\frac{|\beta|}{m_e + m_h} \left[ \left(1 - \cos\left(\frac{4\pi n_0 X_j}{\lambda}\right)\right) \frac{\Delta N_{0,substrate}^2}{N_{active}} \exp(-x/L_{layer}) + \cos\left(\frac{4\pi n_0 X_j}{\lambda}\right) \Delta N_{0,substrate} \exp(-x/L_{substrate}) \right] + \delta \Delta T_{0,surface} \exp(-x/L_{thermal}) \right\} \quad [2]$$

where $\Delta N_{0,substrate}$ and $\Delta T_{0,surface}$ are the substrate 2 excess carrier concentration and excess temperature at x=0, i.e. when the two laser spots are coincident and the offset d=0.

The three decay lengths present in formula [2] have different values. First, it is known that, in a one-dimensional and low modulation frequency problem, $L_{substrate} = \sqrt{D\tau}$ and $L_{thermal} = \sqrt{2D_{th}/\omega_{pump}}$, where D is the carrier diffusivity, $\tau$ is the carrier lifetime, $D_{th}$ is the thermal diffusivity of the substrate 2 and $\omega_{pump}$ is the pump laser beam 7 pulsation, i.e. the modulation of the pump laser power with time. For TP, this typically gives $L_{substrate} \sim 10$ μm and $L_{thermal} \sim 4$ μm in Si. Notice, that the given values are only valid in the one-dimensional case, they are actually shorter in a three-dimensional problem. Second, it can be shown that the decay length $L_{layer}$ of the upper layer 3 plasma component is also shorter than the decay length of the lower layer plasma component 4 $L_{substrate}$. In other words, the thermal component and upper layer 3 plasma component decay faster than the lower layer 4 plasma component. In conclusion, when the distance d between the incident spots of the two laser beams 7,8 is large enough, only the lower layer 4 plasma component remains, i.e:

$$\frac{\Delta R}{R} \to -\frac{4}{n_0^2 - 1} \frac{|\beta|}{m_e + m_h} \cos\left(\frac{4\pi n_0 X_j}{\lambda}\right) \Delta N_{0,substrate} \exp(-x/L_{substrate}) \quad [3]$$

A remark is made concerning the time-dependence of the three signal components. In PMOR techniques such as TP, where the power modulation frequency is relatively high ($\omega\tau \sim 1$), all three components not only have a real part but also an imaginary part to account for their lag with respect to the pump power. This time lag between the pump laser beam 7 and the reflected probe laser beam 8 is responsible for the presence of the two previously mentioned components I (in phase) and Q (90° phase difference) in the reflected probe laser beam 8. In such PMOR techniques only the I signal behaves as shown by formula [3], while the full time dependence needs to be taken into account to explain the lateral behavior of Q. As a consequence, only the I component of the reflected signal 8 is used for teaching the disclosure.

Section 2: Junction Depths of Box-Like Profiles

The theory developed in the previous section is applied to obtain a method for extracting the absolute value of the junction depth $X_j$ of a CVD box-like active doping profile 3 for samples 1 having the same active doping concentration $N_{active}$ but different junction depths $X_j$ as listed in the table I of "Advances in optical carrier profiling through high-frequency modulated optical reflectance" by J. Bogdanowicz, et al. in Journal of Vacuum Science and Technology B, 26 (2008), p. 310-316, hereby incorporated by reference. The obtained results are compared with the measured SIMS junction depths on these samples.

A wafer will typically contain several regions wherein the junction is formed, e.g. different active regions wherein the source/drain junction is formed. Although formed during the same processing steps, the actual doping profile in each of the different regions may vary from one region to another due to process variations. The latter method can be used to determine the relative variations in junction depth $X_j$ e.g. over a part of or over the whole of a wafer. A wafer will typically contain several regions wherein the junction is formed, e.g. different active regions wherein the source/drain junction is formed. Although formed in the same processing steps, the actual doping profile in the different regions may vary from one region to another due to process variations.

The theory developed in the previous section is summarized in formula [3]. This formula [3] is also valid for a reference sample containing layer 4, i.e. the substrate 2 without the upper layer 3 by setting $X_j=0$. Hence one can make the ratio of formula [3] applied to test sample 1 containing a junction region 5 in the substrate 2, in this embodiment in the form of box-like doping profile, and formula [3] applied to an reference sample containing the substrate 2 without the junction region 5, i.e. without the upper layer 3. This ratio $R_a$ is then $$\frac{\Delta R / R^l_{layer}}{\Delta R / R^l_{substrate}} \to \cos\left(\frac{4\pi n_0 X_j}{\lambda}\right) \quad [4]$$

when the laser beam spacing d is large enough. In formula [4], the excess carrier concentration in the lower layer 4 and its decay length are assumed to be independent from the upper layer 3. This is certainly the case if the inactive doping concentration in the upper layer 3 is not too high. The formula [4] express that the ratio of the signals measured respectively on the test sample 1 and on reference sample without the junction 5 is proportional to the junction depth $X_j$ of the test sample 1, if the pump and probe laser 7,8 are sufficiently spaced.

The methods developed in the previous paragraph are applied to the CVD2 and CVD3 matrices listed in the table I of "Advances in optical carrier profiling through high-frequency modulated optical reflectance" by J. Bogdanowicz, et al. in Journal of Vacuum Science and Technology B, 26 (2008), p. 310-316, hereby incorporated by reference. The CVD8 matrix is composed of two series of samples: CVD8-1 and CVD8-2. The CVD8-1 series consists of 6 single CVD layers with almost equal junction depths and different SIMS doping concentrations ranging from about $10^{19}$ to $3\times10^{20}$ cm$^{-3}$. The CVD8-2 series is composed of double layer 3, 4, box-doped structures with the same junction depths, same doping concentration in the shallow 3 layer (about $3\times10^{20}$ cm$^{-3}$) and varying doping concentrations in the second layer 4 ranging from about $3\times10^{19}$ cm$^{-3}$ to $3\times10^{20}$ cm$^{-3}$.

Figure 4:
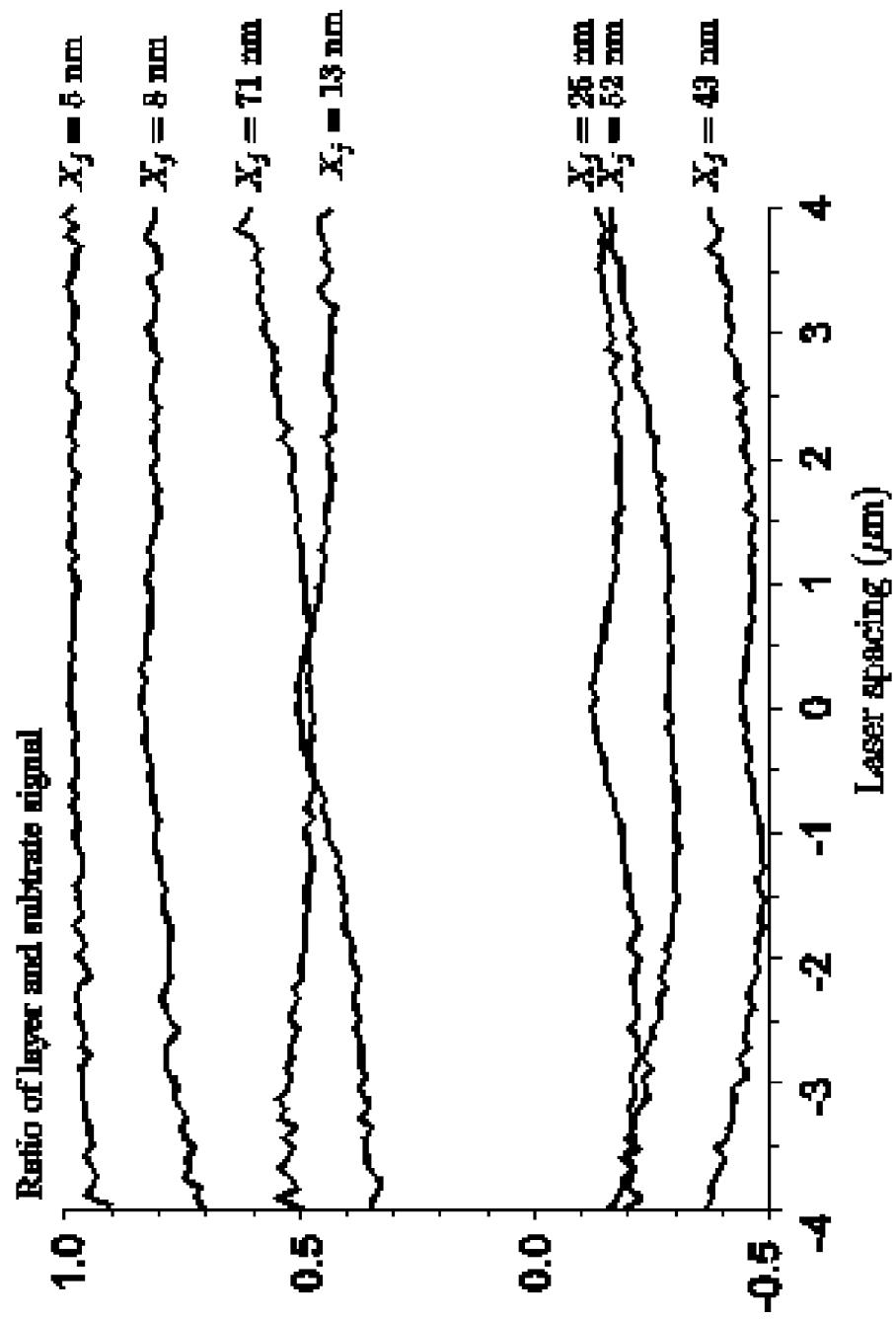
FIG. 4 shows the lateral behavior of the ratio $R_a$ of the PMOR signals obtained on a selection of the samples listed in FIG. 5 according to an experimental embodiment of the present invention. For each of the ratios the corresponding SIMS junction depth is written on the right.

FIG. 4 shows the lateral behavior of the ratio $R_a$ of the PMOR signal $\Delta R/R$ measured on a selection of samples 1 of the CVD2 matrix, listed in the table I of "Advances in optical carrier profiling through high-frequency modulated optical reflectance" by J. Bogdanowicz, et al. in Journal of Vacuum Science and Technology B, 26 (2008), p. 310-316, hereby incorporated by reference, to the PMOR signal $\Delta R/R$ measured on an undoped reference sample, i.e. the substrate 2 without the upper layer 3. For a large majority of the samples 1, the ratio $R_a$ converges to a value between $-1$ and 1. This saturation value is then used to obtain the absolute value of the junction of the test sample 1 using formula 4. Because of the cosine relationship between the ratio $R_a$ and the junction depth $X_j$ as the expressed in formula [4], the effective ratio of the measured PMOR signals should indeed have a value between $-1$ and 1. The fact that the measured ratio obeys this relationship proves that the assumptions made to derive the extraction procedure in section 1 and 2 are indeed correct. One can therefore check the correctness of the method when applied on a particular sample by checking whether the measured ratio $R_a$ of the test sample PMOR signal to the reference sample PMOR signal lies between $-1$ and 1. It is typically for the deepest junctions that the ratio $R_a$ did converge for the used range of the laser spacing d, most likely due to the larger impact of inactive dopants in the upper layer 3 on the substrate 4 level thereby impacting the PMOR signal representative of only the substrate 2.

The unexpected asymmetry of the curves with respect to $x=0$ in FIG. 4 was always observed when performing the PMOR measurement on active doping profiles 3 formed in a silicon substrate 2. This asymmetry can be explained by the introduction of free carriers into the native oxide which is present on the exposed surface of the Si substrate 2 during the PMOR measurement. This native oxide passivates the exposed surface of the silicon substrate 2. In section 4, it is shown that this charging effect can be advantageously used to reduce the sensitivity of the PMOR measurement to the properties of substrate 2 surface thereby making the above developed model more robust leading to enhanced reproducibility and accuracy of the extraction method. Since the offset curves shown in FIG. 4 are obtained by moving the probe laser beam 7 during the PMOR measurement from left to right, the surface which was initially uncharged will become more charged during this scan, such that the PMOR measurement on the left positions (d<0) are done on an essentially uncharged oxide while the PMOR measurement on the right positions (d>0) are done on a charge oxide. Since these PMOR signals are expected to be more reliable, the right part (d>0) of these offset curves is used throughout the further description.

Figure 5:
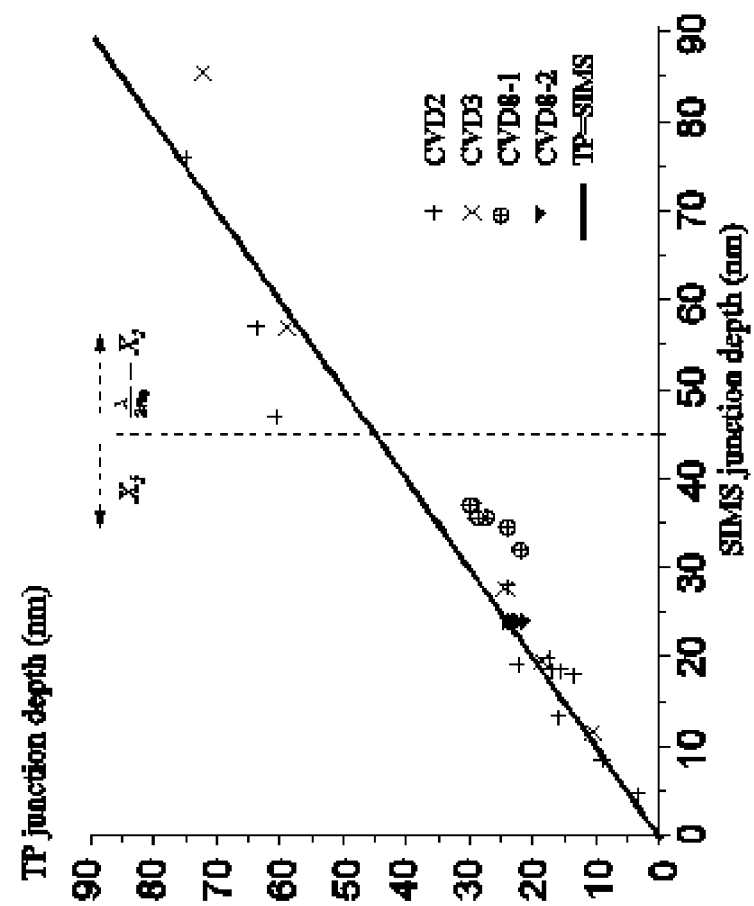
FIG. 5 shows the correlation between the junction depth $X_j$ obtained via SIMS (secondary ion mass spectroscopy) and via the extraction method TP according to an experimental embodiment of the present invention for samples having box-like doping profiles.

FIG. 5 compares the junction depth of the test sample 1 obtained using formula [4] at d=4 μm laser separation with the corresponding junction depth obtained on the test sample 1 using Secondary Ion Mass Spectroscopy (SIMS). The correlation is very good for all samples, even for the double boxes of CVD8-2 with the deeper junctions. Notice however that, due to the periodicity of formula [4], the extraction method cannot distinguish between a junction depth $X_j$ and ($\lambda/2n_0 - X_j$). In FIG. 5 the known SIMS junction depth was therefore used to decide which of both formulas was to be used. This is indicated in FIG. 5 by the vertical dotted line at $X_j=44$ nm. For values of $X_j<44$ nm formula [4] was directly applied. The discrepancies between the value of the junction depth obtained by a method according to this description and the corresponding SIMS junction depth can be explained either by the junction depth non-uniformity over the wafer as the SIMS profile was measured in the centre of the wafer while the extracted junction depths were obtained on other locations on the wafer and/or and by the substrate signal reproducibility as will be discussed in section 4.

The technique has also been tested on the CVD5 and CVD4 samples listed in the table of table I of "Advances in optical carrier profiling through high-frequency modulated optical reflectance" by J. Bogdanowicz, et al. in Journal of Vacuum Science and Technology B, 26 (2008), p. 310-316, which is incorporated herein by reference. However in both cases, the technique gave unacceptable results. In the case of the CVD5 test samples, this is most likely due to the fact that the active doping concentration $N_{active}$ of the upper layer 3 was not high enough, such that $L_{layer} \sim L_{substrate}$ meaning that the layer 3 plasma component did not decay faster than the lower layer 4 plasma component. As a result both plasma components remained present in the PMOR signal and formula [4] could not be used. As for the CVD4 test samples, they contain a very high inactive doping concentration such that the substrate plasma component became dependent on the active doping profile $N_{active}$ such that one assumption made when deriving formula [1] is not valid: $\Delta N_{substrate} < N_{active}$.

Rather than using an undoped substrate, i.e. without the junction 5, as reference sample resulting in formula [4], one can use as reference sample or PMOR measurement a sample or PMOR measurement A also containing a doped layer 3 formed in a same substrate 2 having an active doping profile and characterized by a junction depth $X_j^{reference}$. Preferably the active doping concentration of this reference sample is substantially the same as for the test sample. The ratio $R_a$ of the I-component of the test sample PMOR signal $\Delta R/R_{layer}^I$ to the I component of the reference sample PMOR signal $\Delta R/R_{rreference}^I$ is:

$$\frac{\Delta R/R_{layer}^I}{\Delta R/R_{reference}^I} \rightarrow \frac{\cos\left(\frac{4\pi n_0 X_j}{\lambda}\right)}{\cos\left(\frac{4\pi n_0 X_j^{reference}}{\lambda}\right)}. \quad [5]$$

Formula [5] can be used to derive a method for extracting the relative value of the junction depth of the test sample 1, i.e., the ratio $$\frac{X_j}{X_j^{ref}}.$$

In particular, for $X_j^{reference} < \lambda/(4n_0)$ which is about 44 nm for TP PMOR measurement in Si as discussed in FIG. 5, and if $\Delta X_j = X_j - X_j^{reference}$ is small, formula [5] gives after second-order Taylor expansion of the cosine in the numerator $$\Delta X_j = \frac{\lambda}{4\pi n_0} \left\{ -\tan(4\pi n_0 X_j^{reference}/\lambda) + \text{sign}(\tan(4\pi n_0 X_j^{reference}/\lambda)) \right. \quad [6]$$

$$\left. \sqrt{\tan^2(4\pi n_0 X_j^{reference}/\lambda) + 2\left(1 - \frac{\Delta R/R_{layer}^I}{\Delta R/R_{reference}^I}\right)} \right\},$$

where the sign function is respectively 1 or −1 depending on whether its argument is positive or negative. If e.g. the reference PMOR measurement is taken in the centre of a wafer, formula [6] could be used to determine the junction depth uniformity over a part of the wafer or over the full wafer. Notice that the extraction method disclosed in this paragraph cannot be used with a reference junction depth yielding a zero cosine which would make formula 5 indefinite. In case of a TP PMOR measurement on a silicon substrate 2, such reference junction depth $X_j^{reference}$ would be typically about 22 nm in Si. However if this is the case, because of the dependency of the PMOR signal $\Delta R/R$ on the optical wavelength $\lambda$ of the probe laser beam 8, as shown in formula [4], one can select another optical wavelength $\lambda$ such that the PMOR signal $\Delta R/R_{layer}^I$ obtained on the reference junction $X_j^{reference}$ becomes different from zero. Hence when selecting the parameters of the PMOR measurement the optical frequency of the probe laser beam can be selected to ensure that the PMOR signal is different from zero.

Section 3: Junction Depths of Arbitrary Profiles

In this section, the extension of the disclosed extraction methods to arbitrarily shaped profiles is discussed. In particular, the extension to annealed implanted profiles is discussed. The studied samples are described and fully characterized in particular in the section EXPERIMENTAL of E. Rosseel, et al "Impact of multiple sub-melt laser scans on the activation and diffusion of shallow Boron junctions "IEEE International Conference on Advanced Thermal Processing of Semiconductors, 2008, hereby incorporated by reference in its entirety. Three series of samples were studied implanted uniform over their surface respectively with B only (about 0.5 keV, $10^{15}$ cm-2), with B and Ge (about 12 keV, $5 \times 10^{14}$ cm-2) or with B, Ge and C (about 3 keV, $10^{15}$ cm-2). Samples form all three series were then laser-annealed for different temperatures and different times by scanning for each conditions a laser beam over a part of the surface sample. The temperature of a scan was either about 1220° C. or 1300° C., while duration of the annealing was changed by varying the number of consecutive scans performed on the same area between one to seven times. For each of the three implant series 14 different annealing conditions were obtained which corresponded to 14 different activated junction profiles. As each implant condition was done on a single wafer 2, the substrate signal obtained for the different activated junction profiles should indeed be the same.

The extension of the extraction methods disclosed in sections 1 and 2 to these implanted profiles poses essentially two problems. First, a unique SIMS junction depth was more difficult to define in these implanted profiles due to their finite slope contrary to the box-shaped doping profile of the samples used in sections 1 and 2. It was therefore proposed to take as measure for the junction depth $X_j$ the SIMS junction depth at about $10^{20}$ cm$^{-3}$. Second, as a reference signal without junction 5 was more difficult to obtain, the relative junction extraction method corresponding to formula [6] was preferred above the absolute junction extraction method corresponding to formula [4]. For each series and annealing temperature, the sample which was annealed thrice, i.e. sample "S", usually assumed to be already well activated, is taken as a reference to obtain the reference SIMS junction depth.

Figure 6:
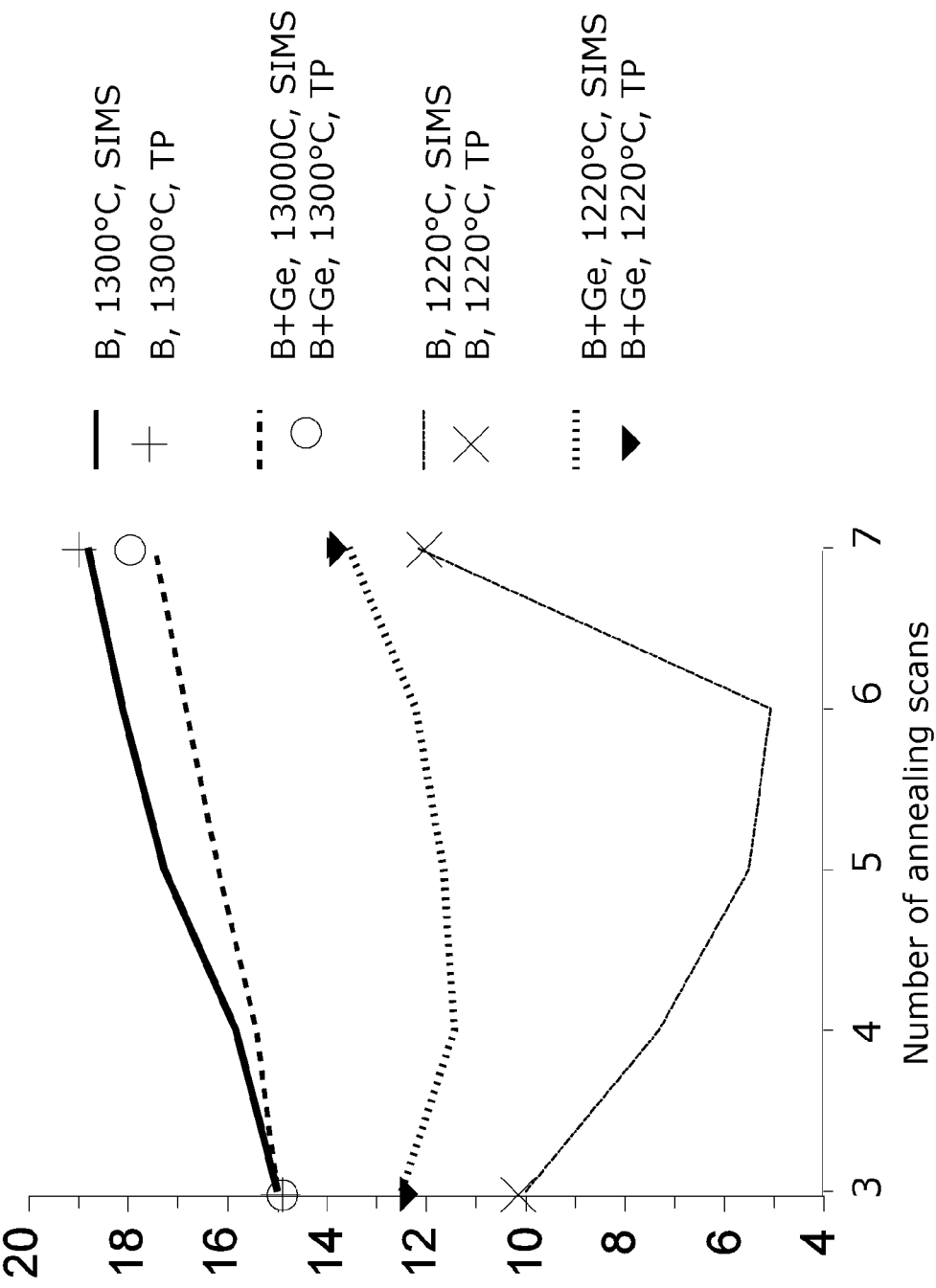
FIG. 6 shows junction depth obtained via an extraction method according to an embodiment of the present invention as function of the number of laser anneal scans for samples having implanted doping profiles.
Figure 7:
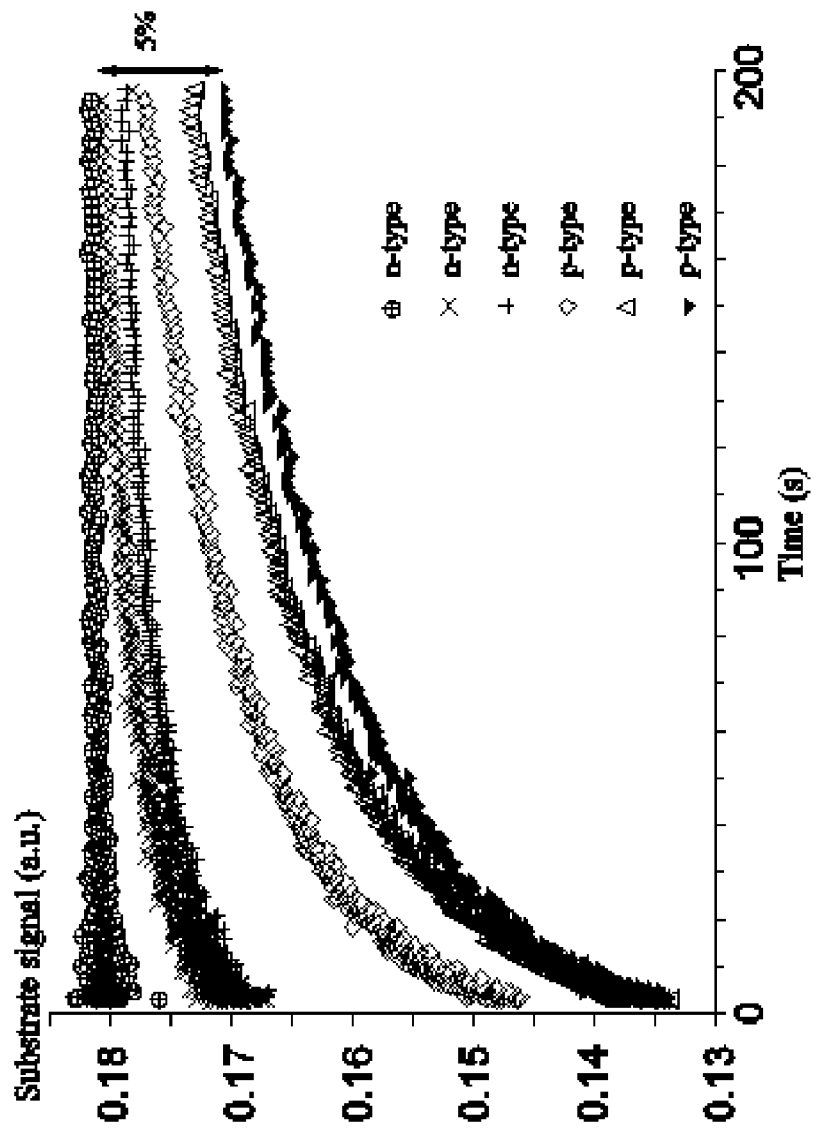
FIG. 7 shows the time-dependency of the PMOR signal due to the passivation of the substrate surface on a series of n-type and p-type doped substrates according to an embodiment of the present invention.

The obtained results are shown in FIG. 6 for the B implanted as well as the B+Ge implanted samples. The relative junction extracted using formula [6] gives a very good agreement with the measured SIMS junction depths. In order to obtain a metric of the absolute value of this extracted junction, the SIMS junction depth is used as reference junction depth in formula [6]. In particular, all curves converge towards the SIMS junction depth measured on the sample which was annealed seven times. Notice the non-monotonic behavior for the low temperature annealing. This does not seem to be physical and could be attributed to the fact that the reference sample (having 3 laser anneal scans) was not sufficiently activated. The C+Ge+B implanted samples give a purely thermal signal as too many defects remained in the substrate 2 even after annealing. These defects have a negative impact on the formation of the plasma components. The present extraction methods are based on the comparison of the substrate/lower layer 4 plasma components of a test sample and of a reference sample. Hence this plasma component must be dominant in each PMOR signal ΔR/R in order to yield useful results.

In summary, this section 3 shows that the procedure can be used and give accurate results for any type of doping profile. Just like for box-like active doping profiles, it can determine the relative junction depth or, if one has an equivalent substrate available for reference, even the absolute junction depth.

Section 4: Accuracy and Reproducibility

In this section, the accuracy and reproducibility of the developed extraction methods are discussed. The accuracy of the methods depends on how well the two major assumptions made when developing the formulas [1] to [6] are verified.

The first major assumption is that at a given laser separation d, the thermal and layer 3 plasma components are negligible with respect to substrate/lower layer 4 plasma component. When using TP on a silicon sample, the thermal component should cause no problem if there are not too many defects in the substrate 2. Similarly, the layer 3 plasma component can be considered to be small enough if the active doping in the upper layer 3 is not too low (>about 5e18 cm$^{-3}$).

The second major assumption is that the lateral behavior of the substrate/lower layer 4 plasma component should be the same on the reference sample and on the unknown test sample. This actually implies two additional requirements. First, it requires that the doping profile N$_{active}$ has little impact on the substrate/lower layer 4 plasma components. This is the case if a sufficient number of doping atoms is activated. The extraction methods disclosed should therefore be preferentially used on well annealed structures. Second it requires that all substrates 2 need to be the same from TP point of view.

To assess the validity of this second requirement, offset curves on 20 different n-type substrates and 20 different p-type substrates were measured. While the PMOR signal variations on n-type substrates were below about 1%, i.e. the measurement accuracy limit, the PMOR signals reach up to about 15% on p-type substrates. The PMOR measurements also showed that the PMOR signal level on n-type substrates was up to about 25% higher than on p-type substrates. This behavior was unexpected from theoretical point of view since the only relevant parameter is the high-injection ambipolar diffusivity which should be independent from the doping type.

Figure 8:
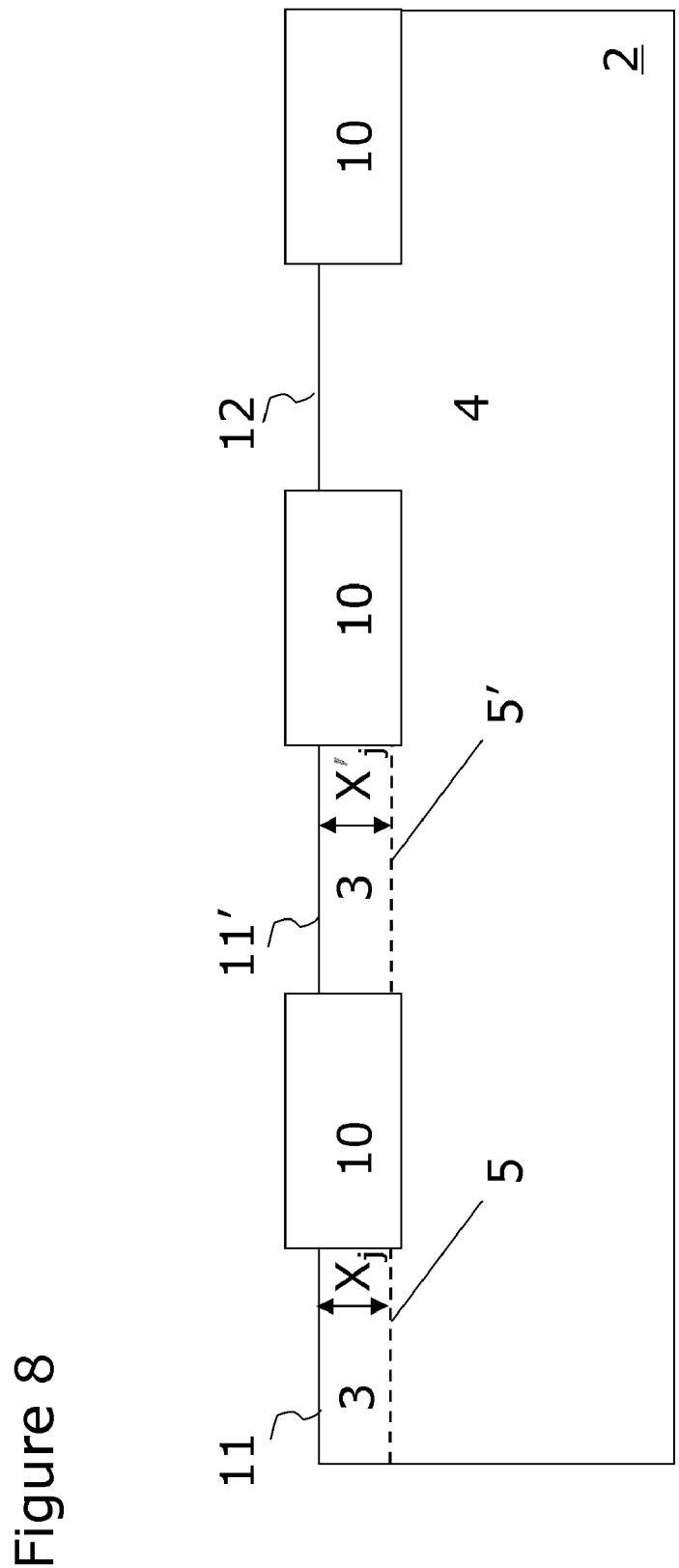
FIG. 8 shows a schematic cross-section of a substrate used in one embodiment to provide a PMOR test sample signal and a PMOR reference sample signal from a single substrate to determine absolute junction depth according to an embodiment of the present invention.

Most of these differences were shown to be due to surface effects. Indeed, if one records the PMOR signal ΔR/R for a certain time, carriers are injected in the surface of the substrate 2 and passivate this surface until the generated electric field between surface and bulk 2 is too high for carriers to be further injected into the surface. This is observed experimentally as a saturation of the signal. It is at saturation that the PMOR signal ΔR/R is the least sensitive to the surface and is therefore more reproducible. FIG. 4 shows that, even though saturation is not reached on all substrates after about 200 s, the difference between the signals on these substrates, whether n- or p-type, is only about 5% (only a selection is shown in FIG. 4). In conclusion, the technique will be more accurate if the surface is passivated. This phenomenon was observed experimentally as a saturation of the PMOR signal ΔR/R over time. It is after saturation that the PMOR signal ΔR/R became the least sensitive to the surface and was therefore more reproducible from on substrate to another. FIG. 8 shows that for a selection of the substrate used, even though saturation was not reached on all substrates after about 200 s, the difference between the signals on these substrates, whether n- or p-type, is only about 5%. One would indeed expect that saturation the PMOR signal should be the same on all type of substrates whatever the doping type. In conclusion, the technique should be more accurate if the surface is passivated in whatever way.

The passivation referred in this paragraph relates to the presence of an electric field at the surface of the substrate to be measured. This passivation technique is sometimes referred to as field-induced passivation. The electrical field reduces the concentration of one carrier type at or near the surface, hence reducing the recombination at the surface where the PMOR measurement is performed. Uncontrolled surface recombination may strongly interfere with the carrier recombination, and hence with the excess carrier concentration, in the underlying layers such as the doped layer 3 and the layer 4 or bulk 2.

This surface electrical field or electrostatic potential barrier may be generated in different ways. One can use an external voltage or one can precharge the surface.

One can use the trapping of free carriers at the surface of the substrate 2 or in a dielectric layer 17 formed thereon as discussed in the previous paragraph. As shown in FIG. 4 the probe laser beam 7 is moved over the surface of the substrate 2 such that not only the PMOR signal ΔR/R is obtained at a location farther away from the place of incidence of the pump laser beam 7, but also the surface is charged more during this laser tracker scan. One can form one or more dielectric layer 19 on this surface which dielectric layers then have an inherent charge density sufficient to prevent recombination near that charged dielectric layer. An example of such charge is AlON which is known to have high negative charge density. One can also reduce the surface recombination.

The surface can also be charged by physical means such as scanning by a laser beam over the surface thereby generating excess carriers in the illuminated substrate 2 for passivating the surface before performing the PMOR measurement on this surface such that the recombination at the surface is under control during the PMOR measurement. If a third laser is provided in the PMOR apparatus this third laser beam can prescan the surface to which the probe laser beam 7 will be focused such that charging of the surface to be measured is done prior to performing a PMOR measurement on this surface. In addition one perform the PMOR measurement in an ambient which dissociates into molecules such that upon providing energy by the third laser beam these molecules will bind to the surface to be scanned by the probe laser beam 7.

One can charge the surface covered with a dielectric layer 19 by using corona charging. United States patent application US 2008 0297189, hereby incorporated by reference teaches the principle of corona charging. By depositing ions generated by corona discharging, a small electrical field is built over the native oxide which prevents the mobile charge carriers to reach the surface. Therefore the bulk lifetime can be measured with a strongly reduced influence of the fast recombination at surface/interface.

One can also reduce the surface recombination by reducing the interface traps, e.g. by chemical passivation with a thermal oxide.

Even without surface passivation, the reproducibility of the substrate signal on different spots of the same wafer was about 1%. The relative determination of the junction depth with respect to e.g. the centre point of a wafer, therefore doesn't require charging of the substrate surface. Hence fast high resolution maps showing the relative variation of the junction depth over an area are therefore feasible.

The wafers used in sections 1 to 3 were not high quality wafers. Measurements on well characterized high-quality device wafers showed a wafer-to-wafer reproducibility of the PMOR signal ΔR/R below about 0.1%, which would make the technique even more accurate when used on such substrates which are used in the effective manufacturing of semiconductor devices.

To asses that the extraction methods can be applied to a given sample, i.e. that the assumptions made are correct, full offset curves can be measured as shown in FIG. 4. The ratio of the signals $$\frac{\Delta R / R_{layer}^l}{\Delta R / R_{reference}^l}$$

should indeed saturate at a value between −1 and 1 when the laser spacing d is sufficiently large.

The reproducibility of the extraction methods can be calculated by measuring the PMOR signal ΔR/R reproducibility on various undoped substrates. A about 5% reproducibility criterion obtained after surface charging on both n-type and p-type substrates was used. The first derivative of formula [3] with respect to junction depth gives $$\Delta X_j = \left| \frac{\partial X_j}{\partial \Delta R / R} \right| \Delta(\Delta R / R) = \frac{1}{\left| \frac{\partial \Delta R / R}{\partial X_j} \right|} \Delta(\Delta R / R) =$$

$$\frac{\lambda}{4\pi n_0} \left| \cot\left(\frac{4\pi n_0 X_j}{\lambda}\right) \right| \frac{\Delta(\Delta R / R)}{\Delta R / R_{substrate}} \leq 0.75 \left| \cot\left(\frac{4\pi n_0 X_j}{\lambda}\right) \right|$$

For substrates the extraction methods have therefore a sub-nm reproducibility for junction depths, which for silicon substrates is in the range of about 10 nm to 35 nm with the current TP630XP set-up of KLA-TENCOR. Notice that these reproducibility values include both the tool reproducibility and wafer-to-wafer reproducibility.

As explained in the previous paragraphs apart from the PMOR signal $\Delta R/R_{layer}^I$ of the sample under test, one need also a second PMOR signal $\Delta R/R_{rreference}^I$ to obtain from the ratio of these two PMOR signals the junction depth $X_j$ of the sample under test. If one wants to determine the absolute value of this junction depth 5, the reference PMOR signal is either only representative of the lower layer 4, i.e. only contains the contribution of the substrate plasma wave component as no junction 5 is present in the substrate 2, or it also representative of the lower layer 4 and the junction 5 but for a known junction depth $X_{j\_reference}$. If one wants to determine the relative value of this junction depth 5, the reference PMOR signal is representative of the lower layer 4 and the junction 5. The reference PMOR signal can be obtained in different ways.

FIG. 8 shows a schematic cross-section of a substrate comprising at least one doped region 11 having a junction 5 with junction depth $X_j$. This substrate can comprise additional doped regions 11' 11 having the junction 5' with junction depth $X'_j$. These regions 11', 11, 12 can be spaced apart by an isolation region 10. When manufacturing semiconductor devices this isolation region 10 is typically the field oxide or shallow trench insulation region. Due to process variations the activated doping profile between these doped regions 11, 11' might vary resulting in a variation of the junction depth $X_j$, $X'_j$ from one region to another. By performing the PMOR measurement on one of this doped regions 11, 11' at an sufficient offset d between the probe 8 and pump 7 laser beam, one obtains a PMOR signal $\Delta R/R_{layer}^I$ in which the layer 3 plasma wave component and the thermal wave component are essentially absent and which substantially depends only on the junction depth $X_j$ and the excess carrier concentration in the underlying layer 4. This substrate further comprises at least one undoped region 12. By repeating the PMOR measurement on one of this undoped regions 12 at an sufficient offset d between the probe 8 and pump 7 laser beam, one obtains a PMOR signal $\Delta R/R_{rreference}^I$ in which the layer 3 plasma wave component and the thermal wave component are essentially absent and which substantially depends only on the excess carrier concentration in the underlying layer 4. The ratio $R_a$ of both PMOR signals will yield the absolute value of the junction depth $X_j$ of the measured doped region 11. In this approach the optical and physical parameters of the substrate 2 determining the PMOR signal are the same for both the reference sample and the test sample as the doped 11 and undoped 12 regions are formed on the same substrate 2.

Figure 9:
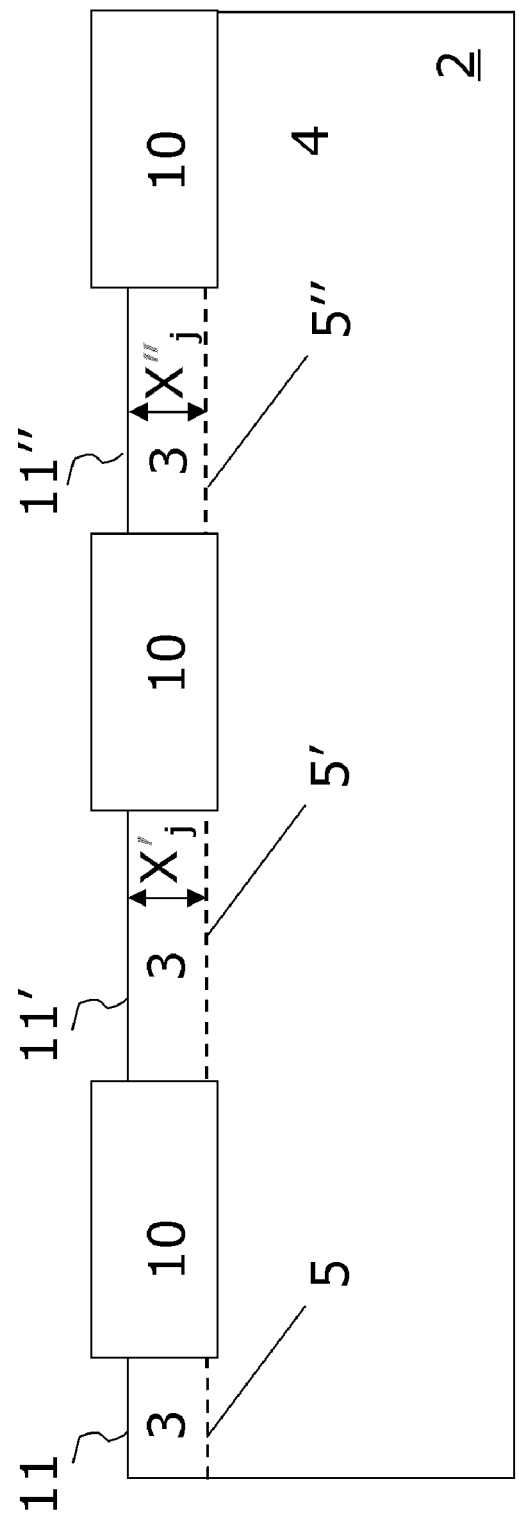
FIG. 9 shows a schematic cross-section of a substrate used in one embodiment to provide a PMOR test sample signal and a PMOR reference sample signal from a single substrate to determine relative junction depth according to an embodiment of the present invention.

FIG. 9 shows a schematic cross-section of a substrate comprising at least one doped region 11 having a junction 5 with junction depth $X_j$. This substrate can comprise additional doped regions 11', 11'' having the junction 5', 5'' with junction depth $X'_j$, $X''_j$. Due to process variations the activated doping profile between these doped regions 11, 11', 11'' might vary resulting in a variation of the junction depth $X_j$, $X'_j$, $X''_j$ one region to another. By performing the PMOR measurement on one of this doped regions 11 at an sufficient offset d between the probe 8 and pump 7 laser beam, one obtains a PMOR signal $\Delta R/R_{layer}^I$ in which the layer 3 plasma wave component and the thermal wave component are essentially absent and which substantially depends only on the junction depth $X_j$ and the excess carrier concentration in the underlying layer 4. By repeating the PMOR measurement on at least one of the doped regions 11', 11'' at an sufficient offset d between the probe 8 and pump 7 laser beam, one obtains a PMOR signal $\Delta R/R_{rreference}^I$ in which the layer 3 plasma wave component and the thermal wave component are essentially absent and which substantially depends only on the junction depth $X'_j$, $X''_j$ the excess carrier concentration in the underlying layer 4. The ratio $R_a$ of both PMOR signals will yield the relative value of the junction depth $X'_j$, $X''_j$ of the other measured doped region 11', 11''. In this approach the optical and physical parameters of the substrate 2 determining the PMOR signal are the same for both the reference sample and the test sample as all doped 11, 11', 11'' are formed on the same substrate 2.

Figure 10:
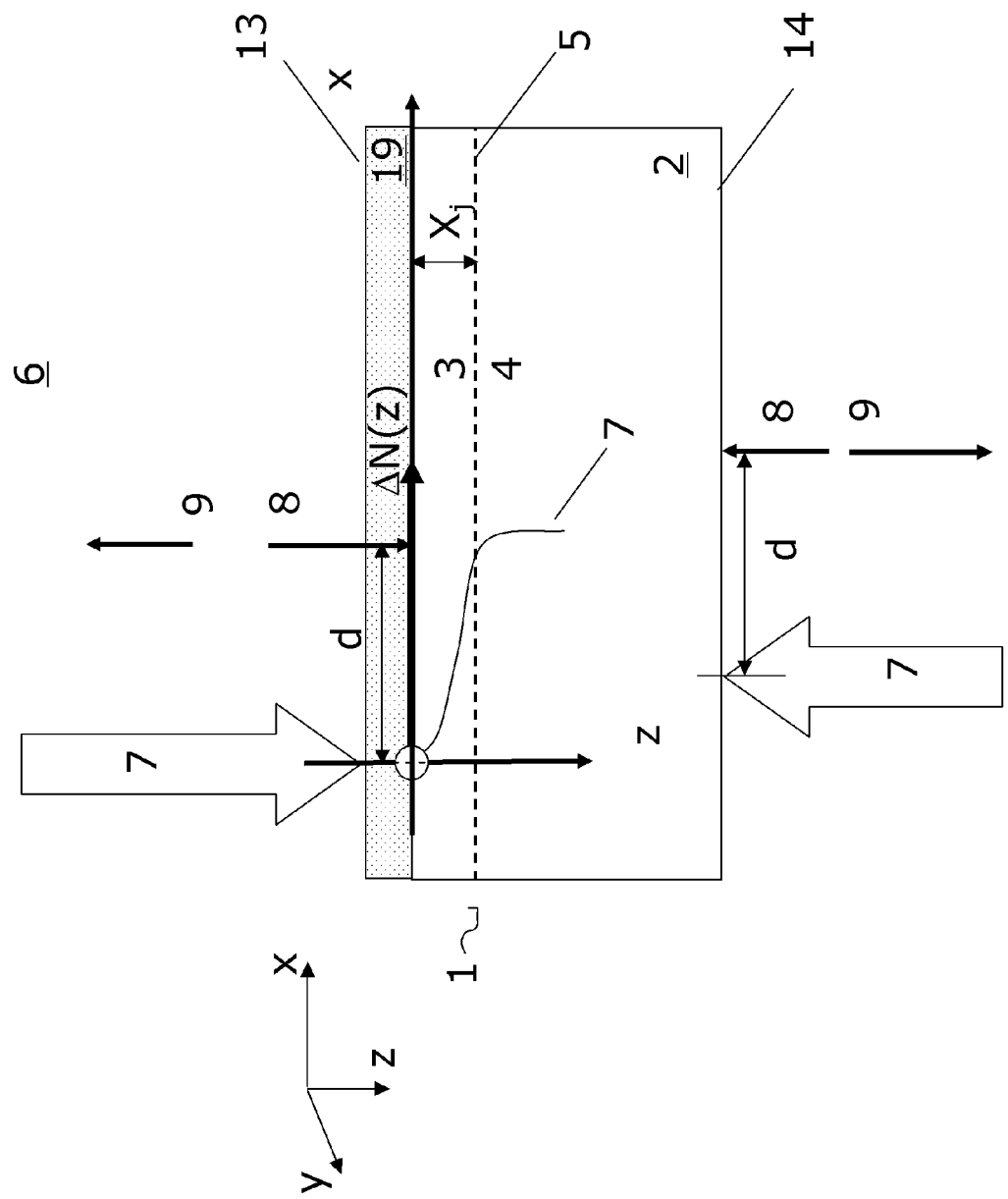
FIG. 10 shows a schematic cross-section of a substrate used in one embodiment to provide a PMOR test sample signal and a PMOR reference sample signal from a single substrate to determine absolute junction depth according to an embodiment of the present invention.

FIG. 10 shows a schematic cross-section of a substrate comprising at least one doped region 11 having a junction 5 with junction depth $X_j$. This doped region 11 is formed at a first main surface 13 of the substrate. One can obtain the reference PMOR signal $\Delta R/R_{rreference}^I$ by performing the PMOR measurement on this surface 13 prior to forming the activated doped layer 3 in the substrate 2. By repeating the PMOR measurement on this surface 13 after the doped layer 3 is formed one obtains the test PMOR signal $\Delta R/R_{layer}^I$. In this approach the optical and physical parameters of the substrate 2 determining the PMOR signal are the same for both the reference sample and the test sample.

In the previous paragraphs the similarity between the substrates wherein the test sample and the reference sample are formed was obtained by forming the test sample and the reference sample on the same substrate, in particular on the same surface 13 of the same substrate 2. Alternatively one can measure the PMOR test signal on the first main surface 13 wherein the doped layer 3 is formed. The PMOR test signal can be measured on another main surface 14 of this substrate 2. FIG. 10 illustrates this approach. Also with this approach the optical and physical parameters of the substrate 2 determining the PMOR signal are the same for both the reference sample and the test sample as the test and reference PMOR signals are obtained from the same substrate 2. By performing the PMOR measurement on the doped region 11 at an sufficient offset d between the probe 8 and pump 7 laser beam, one obtains a PMOR signal $\Delta R/R_{layer}^I$ in which the layer 3 plasma wave component and the thermal wave component are essentially absent and which substantially depends only on the junction depth $X_j$ and the excess carrier concentration in the underlying layer 4 or substrate 2. By repeating the PMOR measurement at an undoped main surface 14 at an sufficient offset d between the probe 8 and pump 7 laser beam, one obtains a PMOR signal $\Delta R/R_{rreference}^I$ in which the layer 3 plasma wave component and the thermal wave component are essentially absent and which substantially depends only on the excess carrier concentration in the substrate 2. The ratio $R_a$ of both PMOR signals will yield the absolute value of the junction depth $X_j$ of the measured doped region 11.

Figure 11:
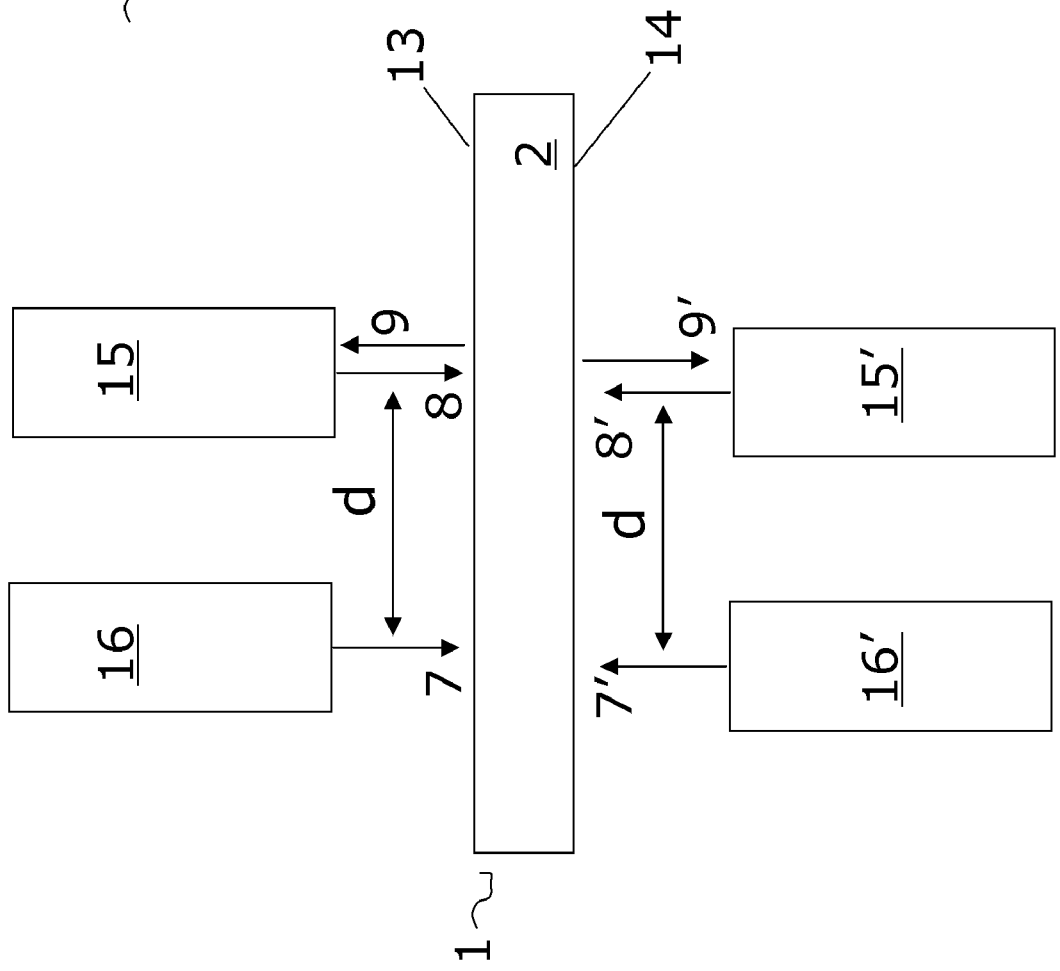
FIG. 11 shows a schematic of a measurement setup used in one embodiment to provide a PMOR test sample signal and a PMOR reference sample signal from a single substrate to determine absolute junction depth according to an embodiment of the present invention.
Figure 12:
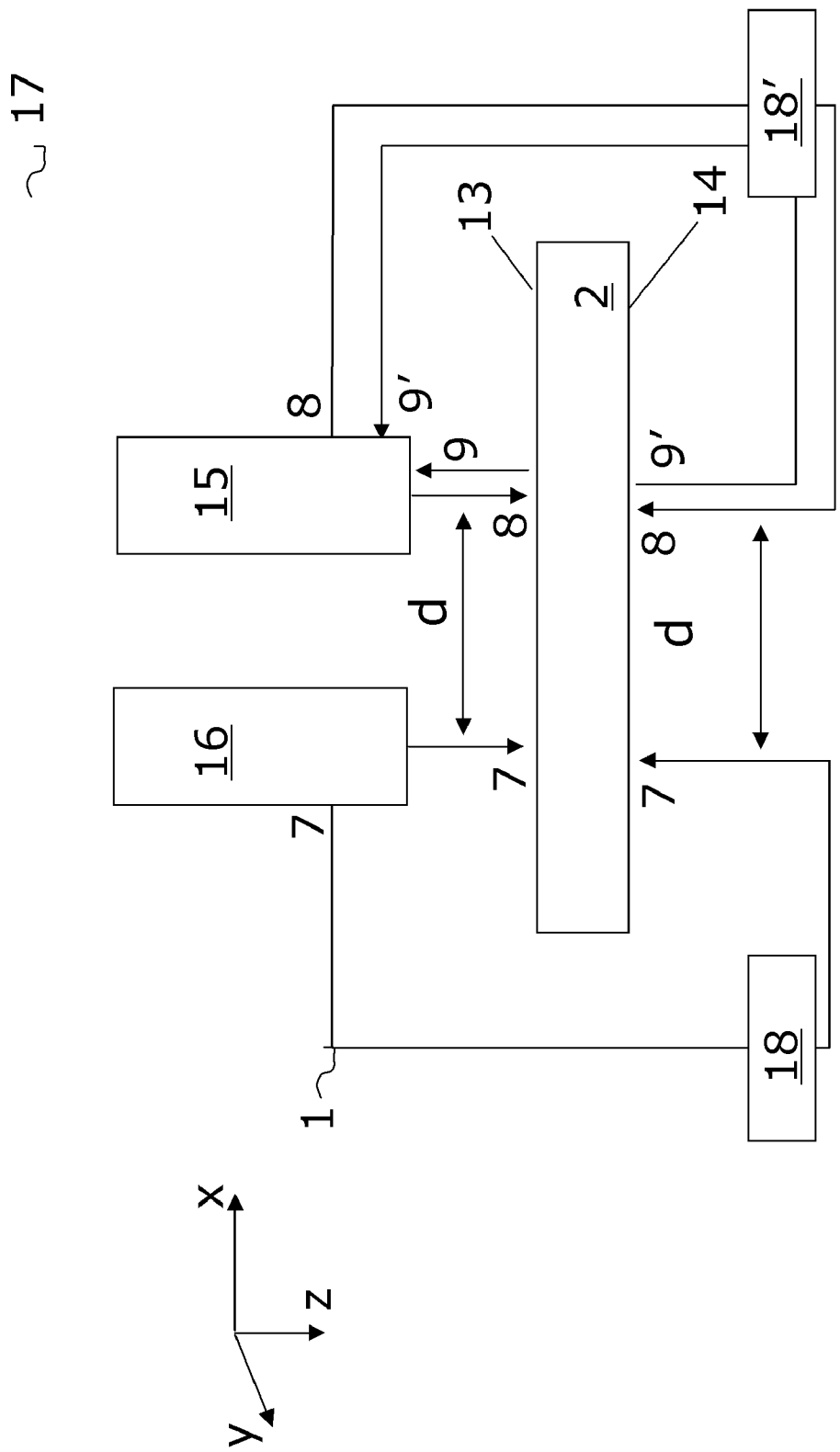
FIG. 12 shows a schematic of a measurement setup used in one embodiment of the present invention to provide a PMOR test sample signal and a PMOR reference sample signal from a single substrate to determine absolute junction depth.

If different surfaces 13, 14 of the substrate are used to generate the respective test and reference PMOR signals, one needs an apparatus 17 capable of providing a pump laser 8, 8' and a probe laser 7,7' beam to these surfaces 13, 14 whereby the same PMOR parameter settings are used. FIGS. 11 and 12 illustrate alternative variations of such an apparatus 17 for determining the absolute value of the depth of a semiconductor junction formed on a first major surface 13 of a substrate whereby the substrate further comprises a second major undoped surface 14. The apparatus 17 comprises a pump laser beam 7 and a probe laser beam 8, means 16 for focusing the pump laser 8 beam to a spot on the first major surface 13 of the substrate 2 thereby modulating in an area surrounding this pump laser beam spot the refractive index profile of the underlying substrate 2, means 15 for focusing the probe laser 7 beam on the first major surface 13 of the substrate 2 at on offset d from the pump laser beam spot, and means for measuring a predetermined characteristic of the probe laser beam 9 reflected by the photomodulated area on the first major surface, wherein the apparatus 17 further comprises means 16 for focusing the pump laser beam 7' and the probe laser beam 8' also to the second major substrate 14, and, means for measuring a predetermined characteristic of the probe laser beam reflected 9' by the photomodulated area on the undoped second major surface 14. The apparatus 17 further comprises means for varying the offset d between the probe laser beam 8, 8' and the pump laser 7, 7' beam at respectively the first doped major surface 13 and the second undoped major surface of the substrate 2.

In FIG. 11 a schematic of such a PMOR apparatus 17 is shown. The apparatus comprises means 15, 16 for generating and focusing a pump laser 7 and probe laser 8 beam to the first doped surface 13 of the substrate 2 and for detecting a PMOR signal 9 generated by this surface 13 upon illumination. The apparatus further comprises means 15', 16' for generating and focusing a pump laser 7' and probe laser 8' beam to the second undoped surface 14 of the substrate 2 and for detecting a PMOR signal 9' generated by this second surface 14 upon illumination.

In FIG. 12 a schematic of an alternative PMOR apparatus 17 is shown. The apparatus comprises means 15, 16 for generating and focusing a pump laser 7 and probe laser 8 beams to the first doped surface 13 of the substrate 2 and for detecting a PMOR signal 9 generated by this surface 13 upon illumination. The apparatus further comprises means 18, 18' for redirecting the pump laser 7 and probe laser 8 beam to the second undoped surface 14 of the substrate 2 and for detecting a PMOR signal 9' generated by this surface 14 upon illumination. By reusing the substrate 2 and the measurement optics and the detection systems 15, 16 to generate and detect the test and reference PMOR signal, the accuracy of the extraction methods according to this disclosure can be further improved.

The foregoing description details certain embodiments of the invention. It will be appreciated, however, that no matter how detailed the foregoing appears in text, the invention may be practiced in many ways. It should be noted that the use of particular terminology when describing certain features or aspects of the invention should not be taken to imply that the terminology is being re-defined herein to be restricted to including any specific characteristics of the features or aspects of the invention with which that terminology is associated.

While the above detailed description has shown, described, and pointed out novel features of the invention as applied to various embodiments, it will be understood that various omissions, substitutions, and changes in the form and details of the device or process illustrated may be made by those skilled in the technology without departing from the spirit of the invention. The scope of the invention is indicated by the appended claims rather than by the foregoing description. All changes which come within the meaning and range of equivalency of the claims are to be embraced within their scope.

What is claimed is:

1. A method of determining a value of a depth of a semiconductor junction of a substrate using a photomodulated optical reflectance measurement technique, the method comprising:
   obtaining a substrate having at least a first region comprising the semiconductor junction;
   obtaining a reference region; and
   performing at least one sequence of:
      i) selecting a set of measurement parameters for the photomodulated optical reflectance measurement,
      ii) measuring on the at least a first region a first optical signal representative of the substrate with the semiconductor junction using the selected set of parameters,
      iii) measuring on the reference region a second optical signal using the selected set of parameters,
      iv) determining the ratio of the first optical signal to the second optical signal, and thereafter extracting from the ratio the depth of the semiconductor junction, wherein the depth of the semiconductor junction is calculated using a function that relates the ratio to the depth of the semiconductor junction.

2. The method of determining the value of the depth of a semiconductor junction according to claim 1, wherein determining the value of the depth of the semiconductor junction comprises determining the absolute value of the depth of the semiconductor junction.

3. The method of determining the value of the depth of a semiconductor junction according to claim 1, wherein the substrate further comprises at least a second region not comprising the semiconductor junction, wherein the reference region is the second region.

4. The method of determining the value of the depth of a semiconductor junction according to claim 1, wherein the second optical signal is measured on the substrate before the junction is formed, and the first optical signal is measured on the substrate after the junction has been formed in the substrate.

5. The method of determining the value of the depth of a semiconductor junction according to claim 1, wherein obtaining the reference region comprises providing another substrate without junction, the optical and semiconducting properties of the other substrate being substantially equal to the substrate with junction, the first optical signal being measured on the substrate with junction, the second optical signal being measured on the substrate without junction.

6. The method of determining the value of the depth of a semiconductor junction according to claim 1, wherein the depth of the semiconductor junction is extracted from the ratio with the formula as follows:

$$X_j = \frac{\cos^{-1}(R_a)\lambda_{probe}}{4\pi n_o}$$

with $X_j$ being the junction depth, $\lambda_{probe}$ being the optical wavelength of a laser beam used for probing the sample, $n_o$ being the refractive index of the substrate in the absence of free carriers and $R_a$ being the ratio of the first optical signal to the second optical signal.

7. The method of determining the value of the depth of a semiconductor junction according to claim 1, wherein the reference region comprises another region of the substrate comprising the semiconductor junction, the another region being different from the first region, and wherein determining the value of the depth of the semiconductor junction comprises determining the relative value of the depth of the semiconductor junction.

8. The method of determining the value of the depth of a semiconductor junction according to claim 1, wherein measuring an optical signal representative of a substrate comprises:
   providing a pump laser beam;
   providing a probe laser beam;
   focusing the pump laser beam to a spot on the substrate, the pump laser beam modulating in an area of the substrate the refractive index profile thereof;
   focusing the probe laser beam to another spot on the substrate; and
   measuring a predetermined characteristic of the probe laser beam reflected by the photomodulated area.

9. The method of determining the value of the depth of a semiconductor junction according to claim 8, wherein the set of parameters comprises an offset d between the two spots on the substrate to which the pump laser beam and the probe laser beam are respectively focused.

10. The method of determining the value of the depth of a semiconductor junction according to claim 9, further comprising: repeating the sequence of processes i) to iv) by selecting another value for the offset d.

11. The method of determining the value of the depth of a semiconductor junction according to claim 10, wherein the sequence of processes i) to iv) is repeated for increasing values of the offset d, until the ratio converges to a value between 1 and −1.

12. The method of determining the value of the depth of a semiconductor junction according to claim 8, wherein measuring a predetermined characteristic of the reflected probe laser beam comprises measuring a component of the reflected probe laser beam which is in phase with the pump laser beam.

13. The method of determining the value of the depth of a semiconductor junction according to claim 1, wherein the junction is formed adjacent to a surface of the substrate, the method further comprising reducing the carrier recombination at the surface, such that during the measurement the first optical signal converges and the second optical signal converges.

14. The method of determining the value of the depth of a semiconductor junction according to claim 1, wherein the substrate is a semiconductor layer.

15. A method of determining a value of a depth of a semiconductor junction of a substrate using a photomodulated optical reflectance measurement technique, the method comprising:

selecting a set of measurement parameters for a photomodulated optical reflectance measurement;

measuring, on a first region comprising a semiconductor junction on a substrate, a first optical signal representative of the substrate with the semiconductor junction using the selected set of parameters;

measuring on a reference region a second optical signal using the selected set of parameters;

determining the ratio of the first optical signal to the second optical signal; and extracting from the determined ratio the depth of the semiconductor junction, wherein the depth of the semiconductor junction is calculated using a function that relates the ratio to the depth of the semiconductor junction.

16. The method of determining the value of the depth of a semiconductor junction according to claim 15, wherein the substrate further comprises at least a second region not comprising the semiconductor junction, wherein the reference region is the second region.

17. The method according to claim 1, wherein obtained a substrate having at least a first region comprising the semiconductor junction comprises annealing the substrate.

18. The method according to claim 1, wherein the measurement parameters are selected to substantially remove a thermal wave component and a layer plasma wave component from the photomodulated optical reflectance measurement.

19. The method according to claim 1, wherein the measurement parameters are selected such that the photomodulated optical reflectance measurement substantially depends only on a substrate plasma wave component.

20. The method according to claim 1, wherein the measurement parameters are selected such that the photomodulated optical reflectance measurement substantially depends only on the depth of the semiconductor junction.

21. The method according to claim 1, wherein the depth of the semiconductor junction is extracted from the ratio based on a formula.

22. A method of determining a value of a depth of a semiconductor junction of a substrate using a photomodulated optical reflectance measurement technique, the method comprising:

obtaining a substrate having at least a first region comprising the semiconductor junction;

obtaining a reference region; and performing at least one sequence of:
   a) selecting a set of measurement parameters for the photomodulated optical reflectance measurement,
   b) measuring on the at least a first region a first optical signal representative of the substrate with the semiconductor junction using the selected set of parameters,
   c) measuring on the reference region a second optical signal using the selected set of parameters,
   d) determining the ratio of the first optical signal to the second optical signal, and thereafter extracting from the ratio the depth of the semiconductor junction, wherein the reference region comprises another region of the substrate comprising the semiconductor junction, the another region being different from the first region, and wherein determining the value of the depth of the semiconductor junction comprises determining the relative value of the depth of the semiconductor junction, wherein the depth of the semiconductor junction is extracted from the ratio with the formula:

$$\frac{\Delta R/R^l_{layer}}{\Delta R/R^l_{reference}} \rightarrow \frac{\cos\left(\frac{4\pi n_0 X_j}{\lambda}\right)}{\cos\left(\frac{4\pi n_0 X_j^{reference}}{\lambda}\right)}$$

with $X_j$ being the junction depth and $X_j^{reference}$ being the junction depth in the reference region, $\lambda$ being the optical wavelength of a laser beam used for probing the sample, $n_o$ being the refractive index of the substrate in the absence of free carriers, $\Delta R/R_{layer}$ being the photomodulated optical reflectance signal in the first region and $\Delta R/R_{reference}$ being the photomodulated optical reflectance signal in the reference region.

* * * * *